(12) United States Patent
Kennedy

(10) Patent No.: US 8,620,451 B2
(45) Date of Patent: Dec. 31, 2013

(54) THERAPY DEVICE AND SYSTEM AND METHOD FOR REDUCING HARMFUL EXPOSURE TO ELECTROMAGNETIC RADIATION

(75) Inventor: John Kennedy, Guelph (CA)

(73) Assignee: Syneron Beauty Inc. (CA)

( * ) Notice: Subject to any disclaimer, the term of this patent is extended or adjusted under 35 U.S.C. 154(b) by 1259 days.

(21) Appl. No.: 11/383,812

(22) Filed: May 17, 2006

(65) Prior Publication Data

US 2007/0185553 A1    Aug. 9, 2007

(30) Foreign Application Priority Data

Feb. 6, 2006   (CA) ...................................... 2535276

(51) Int. Cl.
    *A61N 5/00* (2006.01)
(52) U.S. Cl.
    USPC ....................................................... 607/101
(58) Field of Classification Search
    USPC ....................................................... 607/101
    See application file for complete search history.

(56) References Cited

U.S. PATENT DOCUMENTS

| | | |
|---|---|---|
| 2,183,726 A | 2/1939 | Sommer et al. |
| 2,231,095 A | 2/1941 | Sommer et al. |
| D269,294 S | 6/1983 | Rakocy et al. |
| D271,015 S | 10/1983 | Geraets |
| D271,199 S | 11/1983 | Geraets |
| D274,462 S | 6/1984 | Rakocy et al. |
| 4,553,936 A | 11/1985 | Wang |
| 4,753,958 A | 6/1988 | Weinstein et al. |
| 4,784,135 A | 11/1988 | Blum et al. |
| 4,867,682 A | 9/1989 | Hammesfahr et al. |
| 5,169,384 A | 12/1992 | Bosniak et al. |
| 5,286,479 A | 2/1994 | Garlich et al. |
| 5,316,473 A | 5/1994 | Hare |
| 5,402,697 A | 4/1995 | Brooks |
| 5,418,130 A | 5/1995 | Platz et al. |
| 5,487,662 A | 1/1996 | Kipke et al. |
| 5,521,392 A | 5/1996 | Kennedy et al. |
| 5,611,793 A | 3/1997 | Wilson et al. |

(Continued)

FOREIGN PATENT DOCUMENTS

| | | |
|---|---|---|
| CA | 2495005 A1 | 2/2004 |
| CN | 1078383 A | 11/1993 |

(Continued)

OTHER PUBLICATIONS

Cohen L.R., "What causes bad breath?", University of Toronto; webpage (printed before Nov. 2, 2004).

(Continued)

*Primary Examiner* — Linda Dvorak
*Assistant Examiner* — Kaitlyn Smith
(74) *Attorney, Agent, or Firm* — Smith Risley Tempel Santos LLC; Gregory Scott Smith

(57) ABSTRACT

The invention is directed to a therapy device, including a body, an energy source disposed on the body for emitting a desired wavelength of electromagnetic radiation, and a proximity sensor for sensing proximity of the device to a desired surface. Also disclosed are a material dispensing system disposed on the body for dispensing a desired material for use with the device and accessories and compositions used with the therapy device, including interchangeable energy source-containing heads and interchangeable material containers. Methods for using the therapy device are also disclosed.

19 Claims, 20 Drawing Sheets

(56) References Cited

U.S. PATENT DOCUMENTS

| | | | |
|---|---|---|---|
| 5,628,771 A * | 5/1997 | Mizukawa et al. | 607/102 |
| 5,642,997 A | 7/1997 | Gregg et al. | |
| 5,658,148 A | 8/1997 | Neuberger et al. | |
| 5,698,866 A | 12/1997 | Doiron et al. | |
| 5,814,008 A | 9/1998 | Chen et al. | |
| 5,824,023 A | 10/1998 | Anderson | |
| 5,993,180 A | 11/1999 | Westerhof et al. | |
| 6,056,548 A | 5/2000 | Neuberger et al. | |
| 6,063,108 A | 5/2000 | Salansky et al. | |
| 6,080,127 A | 6/2000 | Li et al. | |
| 6,080,391 A | 6/2000 | Tsuchiya et al. | |
| 6,107,326 A | 8/2000 | Jori | |
| 6,132,701 A | 10/2000 | Perez et al. | |
| 6,190,609 B1 | 2/2001 | Chapman et al. | |
| 6,191,110 B1 | 2/2001 | Jaynes et al. | |
| 6,221,095 B1 | 4/2001 | Van Zuylen et al. | |
| 6,231,593 B1 | 5/2001 | Meserol | |
| 6,251,127 B1 | 6/2001 | Biel | |
| 6,258,319 B1 | 7/2001 | Hearst et al. | |
| 6,273,884 B1 * | 8/2001 | Altshuler et al. | 606/9 |
| 6,308,413 B1 | 10/2001 | Westerhof et al. | |
| 6,343,400 B1 | 2/2002 | Massholder et al. | |
| 6,343,933 B1 | 2/2002 | Montgomery et al. | |
| 6,353,763 B1 * | 3/2002 | George et al. | 607/50 |
| 6,433,343 B1 | 8/2002 | Cimino et al. | |
| 6,461,567 B1 | 10/2002 | Hearst et al. | |
| 6,462,070 B1 | 10/2002 | Hasan et al. | |
| 6,471,716 B1 | 10/2002 | Pecukonis | |
| 6,487,447 B1 | 11/2002 | Weimann et al. | |
| 6,493,940 B2 | 12/2002 | Westerhof et al. | |
| 6,494,900 B1 | 12/2002 | Salansky et al. | |
| 6,497,702 B1 | 12/2002 | Bernaz | |
| 6,508,813 B1 | 1/2003 | Althshuler | |
| 6,511,475 B1 * | 1/2003 | Altshuler et al. | 606/9 |
| 6,514,243 B1 | 2/2003 | Eckhouse et al. | |
| 6,517,532 B1 | 2/2003 | Altshuler et al. | |
| 6,533,775 B1 | 3/2003 | Rizoiu et al. | |
| 6,558,653 B2 | 5/2003 | Andersen et al. | |
| 6,572,637 B1 | 6/2003 | Yamazaki et al. | |
| 6,594,905 B2 | 7/2003 | Furst et al. | |
| 6,602,245 B1 | 8/2003 | Thiberg | |
| 6,612,819 B1 | 9/2003 | Furst et al. | |
| 6,632,002 B1 | 10/2003 | Chubb et al. | |
| 6,663,620 B2 | 12/2003 | Altshuler et al. | |
| 6,676,655 B2 | 1/2004 | McDaniel | |
| D490,156 S | 5/2004 | Fischer et al. | |
| D490,526 S | 5/2004 | Jonsen | |
| 6,780,838 B2 | 8/2004 | Lipton et al. | |
| RE38,634 E | 10/2004 | Westerhof et al. | |
| 6,887,260 B1 | 5/2005 | McDaniel | |
| 7,077,840 B2 * | 7/2006 | Altshuler et al. | 606/9 |
| 7,935,107 B2 * | 5/2011 | Altshuler et al. | 606/9 |
| 2001/0007068 A1 * | 7/2001 | Ota et al. | 606/9 |
| 2002/0183245 A1 | 12/2002 | Hasan et al. | |
| 2002/0198575 A1 | 12/2002 | Sullivan | |
| 2003/0032900 A1 * | 2/2003 | Ella | 601/6 |
| 2003/0055414 A1 * | 3/2003 | Altshuler et al. | 606/9 |
| 2003/0195494 A1 | 10/2003 | Altshuler et al. | |
| 2003/0199946 A1 | 10/2003 | Gutwein | |
| 2004/0147984 A1 * | 7/2004 | Altshuler et al. | 607/88 |
| 2006/0149343 A1 * | 7/2006 | Altshuler et al. | 607/90 |
| 2006/0271028 A1 * | 11/2006 | Altshuler et al. | 606/9 |
| 2007/0038206 A1 * | 2/2007 | Altshuler et al. | 606/20 |
| 2007/0198004 A1 * | 8/2007 | Altshuler et al. | 606/9 |
| 2007/0213696 A1 * | 9/2007 | Altshuler et al. | 606/9 |
| 2007/0239142 A1 * | 10/2007 | Altshuler et al. | 606/9 |
| 2007/0239143 A1 * | 10/2007 | Altshuler et al. | 606/9 |
| 2008/0139901 A1 * | 6/2008 | Altshuler et al. | 600/306 |
| 2009/0234341 A1 * | 9/2009 | Roth | 606/9 |
| 2009/0234342 A1 * | 9/2009 | Ely et al. | 606/9 |
| 2010/0063565 A1 * | 3/2010 | Beerwerth et al. | 607/88 |
| 2010/0274329 A1 * | 10/2010 | Bradley et al. | 607/90 |

FOREIGN PATENT DOCUMENTS

| | | |
|---|---|---|
| EP | 0743029 B1 | 7/2002 |
| EP | 0824019 B1 | 11/2002 |
| GB | 2125986 A | 8/1982 |
| GB | 2202442 A | 9/1988 |
| JP | 04299998 A2 | 10/1992 |
| JP | 06113920 A2 | 4/1994 |
| JP | 11132843 A2 | 5/1999 |
| JP | 2003034630 | 2/2003 |
| WO | WO 93/21992 A1 | 11/1993 |
| WO | WO9909143 A1 | 2/1999 |
| WO | WO02078644 A2 | 10/2002 |
| WO | WO 02094116 A1 * | 11/2002 |
| WO | WO03039367 A1 | 5/2003 |

OTHER PUBLICATIONS

Elman M. et al., "The effective treatment of acne vulgaris by a high-intensity, narrow bank 405-420 nm light source", Cosmetic & Laser Ther 2003; 5: 111-116.

Friedberg J.S. et al., "Antibody-Targeted Photolysis Bacteriocidal Effects of Sn (IV) Chlorin e6-Dextran-Monoclonal Antibody Conjugates", Annals New York Academy of Sciences 618:383-393, 1991.

Greenstein G., Full-mouth therapy versus individual quadrant root planning: a critical commentary, J Periodontol Jul. 2002;73(7):797-812 (Abstract).

Matevski D. et al., "Lethal photosensitization of periodontal pathogens by a red-filtered Xenon lamp in invitro", J. Periodont. Res. 2003, 38:428-435.

Matevski D. et al., "Sensitivity of Porphyromonas gingivalis to Light-Activated Toluidine Blue O", University of Toronto, Faculty of Dentistry; Slide presentation (presented before Nov. 15, 2002).

Morton C.A. et al., An open study to determine the efficacy of blue light in the treatment of mild to moderate acne: preliminary data (publication status unknown).

Wainwright M., Photodynamic antimicrobial chemotherapy (PACT), Journal of Antimicrobial Chemotherapy (1998) 42, 13-28.

Ondine Biopharma web page—printed Oct. 15, 2002.

Quirynen, M. et al., "The intra-oral translocation of periodontopathogens jeopardises the outcome of periodontal therapy", Journal of Clincial Periodontology, Jun. 2001, vol. 28, Issue 6, p. 499 (Abstract).

De Soete, M. et al., "One-stage full-mouth disinfection. Long-term microbiological results analyzed by checker board DNA-DNA hybridization", J Periodontol Mar. 2001; 72(3):374-82 (Abstract).

Bollen, CM. et al., "The effect of a one-stage full-mouth disinfection on different intra-oral niches. Clinical and microbiological observations", J Clin Periodontol Jan. 1998;25(1):56-66 (Abstract).

Bollen, CM. et al., "Full- versus partial-mouth disinfection in the treatment of periodontal infections. A pilot study: long-term microbiological observations", J Clin Periodontol Oct. 1996;23(10):960-70 (Abstract).

Hamblin, M. et al., "Rapid Control of Wound Infections by Targeted Photodynamic Therapy Monitored by In Vivo Bioluminescence Imaging", Photochemistry and Photobiology, 2002, 75(1): 51-57.

Malik, Z. et al., "New Trends in Photobiology (Invited Review) Bactericidal Effects of Photoactivated Porphyrins—An Alternative Approach to Antimicrobial Drugs", Journal of Photochemistry and Photobiology, B: Biology, 5 (1990) 281-293.

Mongardini, C. et al., "One stage full- versus partial-mouth disinfection in the treatment of chronic adult or generalized early-onset periodontitis. I. Long-term clinical observations", J Periodontol Jun. 1999;70(6):632-45 (Abstract).

Quirynen, M. et al., "The role of chlorhexidine in the one-stage full-mouth disinfection treatment of patients with advanced adult periodontitis. Long-term clinical and microbiological observations", J Clin Periodontol Aug. 2000;27(8):579-89 (Abstract).

Quirynen, M. et al., "One stage full- versus partial-mouth disinfection in the treatment of chronic adult or generalized early-onset periodontitis. II. Long-term impact on microbial load", J Periodontol Jun. 1999;70(6):646-56 (Abstract).

(56) References Cited

OTHER PUBLICATIONS

Quirynen, M. et al., "The effect of a 1-stage full-mouth disinfection on oral malodor and microbial colonization of the tongue in periodontitis. A pilot study", J Periodontol Mar. 1998;69(3):374-82 (Abstract).

Quirynen, M. et al. "Full- vs. partial-mouth disinfection in the treatment of periodontal infections: short-term clinical and microbiological observations", J Dent Res Aug. 1995;74(8):1459-67 (Abstract).

Spire Awarded Contract for Ear Surgery Laser—Press Release Aug. 23, 2002.

Vandekerckhove, BN. et al., "Full- versus partial-mouth disinfection in the treatment of periodontal infections. Long-term dinical observations of a pilot study", J Periodontol Dec. 1996;67(12):1251-9 (Abstract).

Coventry et al. (2000) "ABC of oral health: Periodontal disease" British Medical Journal, 321, 36-39.

Krespi, et al. (2005) "Lethal photosensitization of oral pathogens via red-filtered halogen lamp" Oral Diseases, 11(S1), 92-95.

Komerik et al. (2003) "In vivo killing of Porphyromonas gingivalis by toluidine blue-mediated photosensitization in an animal model" Antimicrobial Agents and Chemotherapy, 47(3), 932-940.

Meisel et al. (2005) "Photodynamic therapy for periodontal diseases: State of the are" J. Photochem. Photobiol., 79, 159-170.

Nakano et al. (2002) "Correlation between oral malodor and periodontal bacteria" Microbes Infect., 4(6), 679-683.

Sanz et al. (2001) "Fundamentals of breath malodour" Journal of Contemporary Dental Practice, 2(4), 1-13.

Sarkar et al. (1993) "Lethal photosensitization of bacteria in subgingival plaque from patients with chronic periodontitis" J. Periodont. Res., 28, 204-210.

Soukos et al. (1998)"Targeted antimicrobial photochemotherapy", Antimicrobial Agents and Chemotherapy 42(10), 2595-2601.

Wilson et al. (1995) "Bacteria in supragingival plaque samples can be killed by low-power laser light in the presence of a photosensitizer" J. Appl. Bacteriol., 78, 569-574.

Wilson (2005) "Lethal photosensitisation of oral bacteria and its potential application in the photodynamic therapy of oral infection" Photochem. Photobiol. Sci., 3, 412-418.

Wood, et al. (1999) "An in vitro study of the use of photodynamic therapy for the treatment of natural oral plaque biofilms formed in vivo" J. Photochem. Photogiol. B: Biol., 50, 1-7.

Acne Clearance, LHE Clinical Casebook, Radiancy: Lighting the Future of Skin Care, © 2002.

Acne Star web page, describing Clinical Studies, "The Treatment of acne vulgaris with a novel device that uses Gallium-Nitride diode light", printed May 5, 2005.

Acne Star web page, describing "How to use get rid of Acne Treatment", printed May 5, 2005.

Aesthetic Buyers Guide: The Leading Cosmetic Practice Resource, Jan./Feb. 2004, vol. 7, No. 1.

Calderhead, R. Glen, "The Photobiology of LED Phototherapy".

Flow Control Network web page, "Mini Diaphragm Pumps for Precision Dispensing" by Ping Lin, printed Aug. 2, 2005.

Pharmaceutical description, Levulan® Kerastick aminolevulinic acid HCI) for Topical Solution, 20%.

Skin911.com web page regarding Peter Thomas Roth Clinical Acne Medication, acne treatment-Benzoyl Peroxide 5% pbp5, printed Apr. 19, 2005.

Temperatures.com web page, "Thermistor Temperature Sensors," printed Aug. 2, 200.

www.lightbioscience.com web page, GentleWaves Cosmeceuticals, printed Jul. 29, 2005.

www.lightbioscience.com web page, GentleWaves LED Photomodulation Fact Sheet, printed Jul. 29, 2005.

Search results from Delphion web site, dated Nov. 22, 2005.

\* cited by examiner

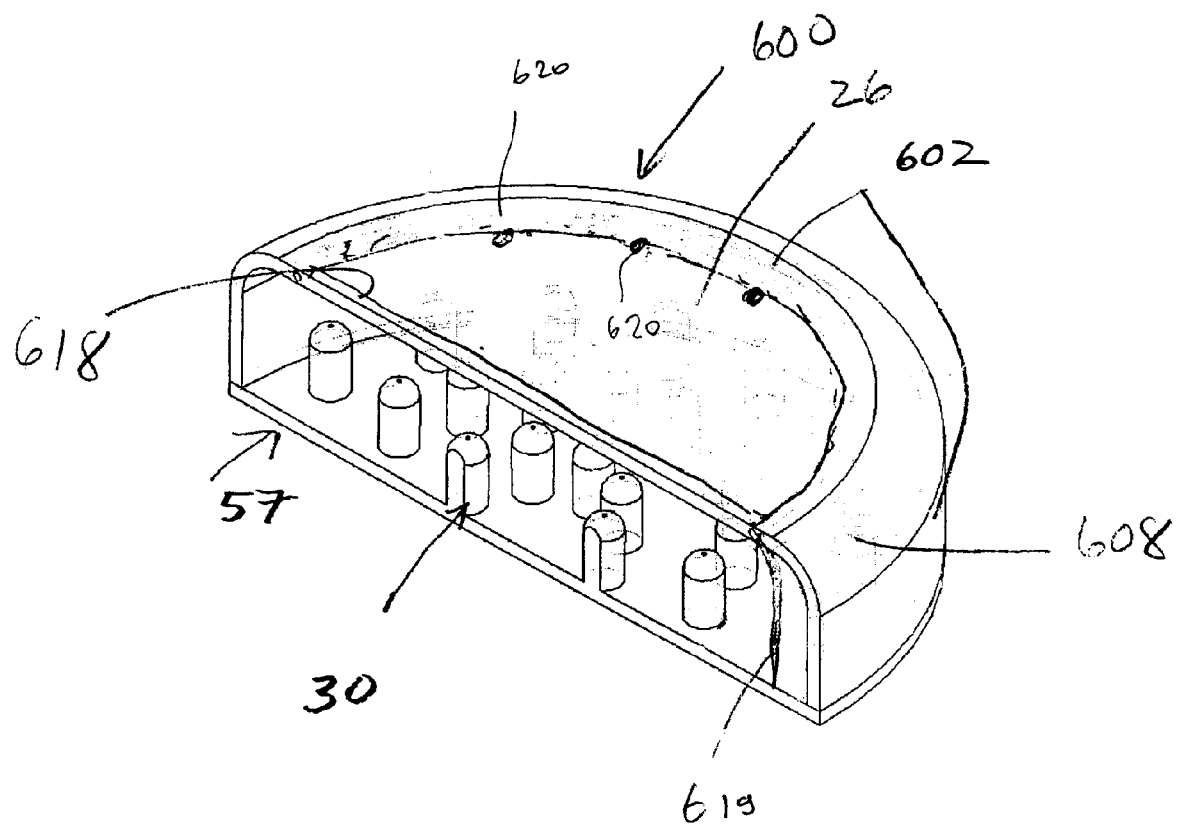

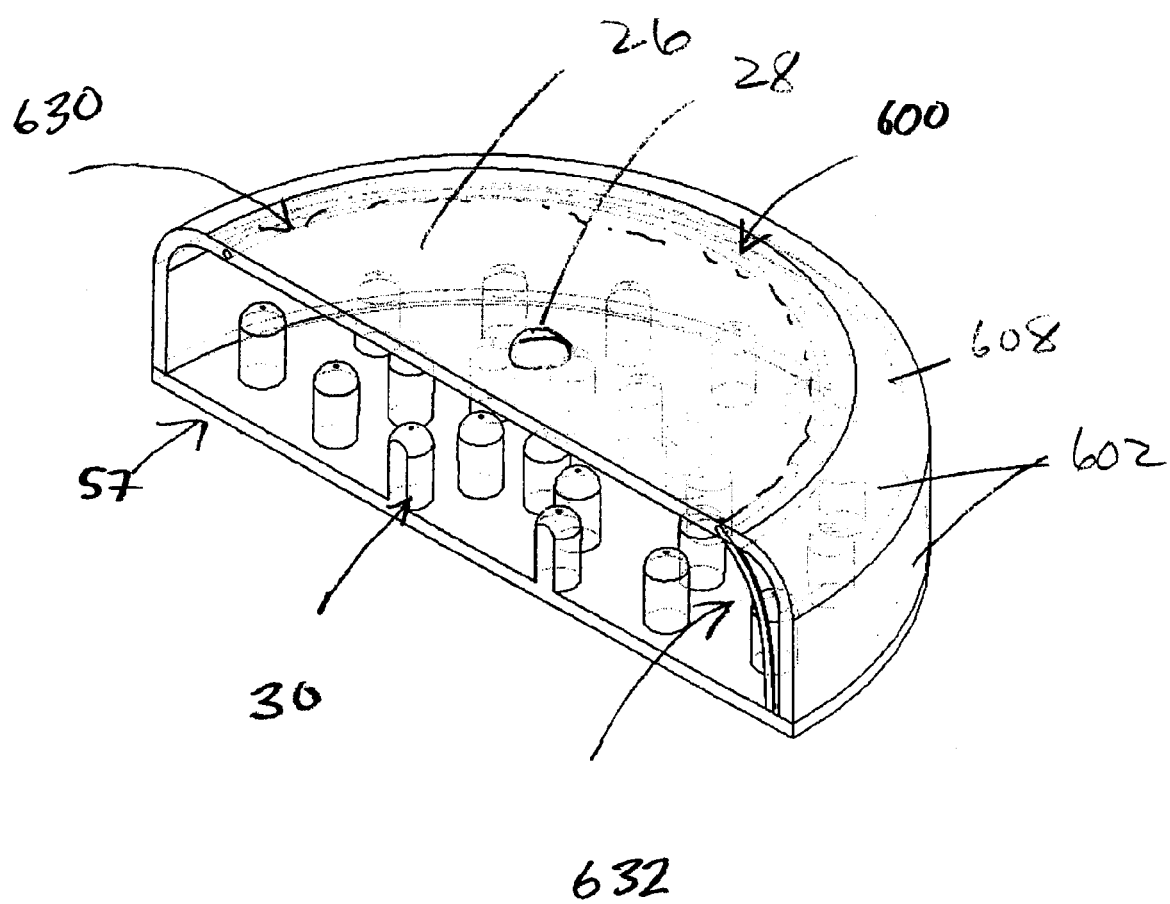

THERAPY DEVICE AND SYSTEM AND METHOD FOR REDUCING HARMFUL EXPOSURE TO ELECTROMAGNETIC RADIATION

FIELD OF THE INVENTION

This invention relates to therapy devices and in particular to handheld devices for administering therapy using electromagnetic radiation.

BACKGROUND OF THE INVENTION

Therapy using electromagnetic radiation has been used to treat soft tissue injuries such as capsulitis, bursitis, sprains, strains, hematomas and tendinitis, acute and chronic joint problems such as osteoarthritis, rheumatoid arthritis and ligament and tendon injuries, tendinitis, arthritic pain, chronic pain such as post herpetic neuralgia, chronic back and neck pain, metatarsalgia, trigeminal neuralgia, brachial neuralgia, plantar fisciitis, cellular damage, in vitro fertilization enhancement, stimulation of embryogenesis, soft tissue injury, aging skin, seasonally affected disorder, inflammation, fine lines and wrinkles, mucositis, frozen shoulder, temporomandibular joint diseases and disorders (TMJ) and carpal tunnel syndrome.

Therapy using electromagnetic radiation has also been used to treat non-union and small bone fractures, herpes, apthous ulcers, leg ulcers, dermatitis, wound healing, burns, acute epididymitis, otorhinolaragngology, gynecology, obstetrics, superficial AP stimulation and tonification, cosmetic imperfections, cellulite, and acne, among other things.

Typically, treatment or therapy using electromagnetic radiation involves radiating energy onto or into a patient's skin. The radiation is typically applied at wavelengths either in the visible, ultraviolet, radiofrequency, or the infrared range. A wide variety of radiating energy sources are available and known in the art. The radiating energy sources used in these therapies radiate energy at a wide variety of wavelengths with different wavelengths having been found to be useful depending on the ailment being treated.

Acne vulgaris is one of the world's most common skin conditions and results from blockage, bacterial colonization and inflammation of the sebaceous follicles. The main cause of acne stems from an abnormally high amount of bacteria, mainly *propionibacterium acnes* (*P. acnes*), resulting in inflammatory acne. Acne affects between 85-100% of young adults up to the age of 24 years and up to 50% of adults 25 and older. It usually appears on the face, chest, back and limbs and can produce life-long scars, both emotionally and physically. In the United States alone over 17,000,000 people actively seek acne treatment on an ongoing basis. These treatments consist of professionally prescribed pharmaceuticals, cosmeceuticals and invasive skin resurfacing. The *P. acnes* bacteria has developed up to 80% resistance to antibiotics commonly used to treat acne in the past.

*acnes* absorbs light from the ultraviolet region to about 430 nm, and also absorbs light at about 630 nm. Blue light phototherapy works for a majority of patients with *P. Acne* vulgaris. The bacteria is made up of an endogenous porphyrin which is a naturally occurring photosensitizer. This photosensitizer absorbs the blue light energy between about 405 to about 425 nanometers and forms a singlet oxygen which simply destroys the bacteria cell. No systemic drugs with their potential side effects and invasive procedures requiring long healing times are necessarily used. For example, radiating energy sources having a peak wavelength of about 415 nm and a bandwidth of about 20 nm have been found particularly useful in the treatment of acne. Peak wavelengths of about 630 nm have also been useful in this regard.

Other examples of electromagnetic radiation useful for treatments include radiation at wavelengths of about 800-810 nm for leg vein and hair removal, wart treatments, hair growth stimulation and tattoo removal, wavelengths of about 1064 nm for skin peel and hair reduction, and of about 574 nm for wrinkle reduction. Varying treatment regimens of pulsing wave (PW) or continuous wave (CW) light, at varying energy levels, are known in the art. Typically, these treatments utilize wavelengths between about 250 and about 2000 nm.

Hand-held therapy devices for delivering electromagnetic radiation are known in the art, however, they are quite expensive and typically limited to one specific use (and one specific wavelength spectrum). The increasing use by medical professionals of different types of electromagnetic radiation devices for a broad range of indications has driven the market demand for similar type devices. Unlike use in a medical setting, the manufacturers of such devices are unable to insure that users follow safety instructions and utilize safety equipment, such as eye protection, provided.

Accordingly, there is a need for a device for delivering radiation that is flexible enough to provide a variety of treatment regimens and wavelength spectrums, so that the device can be used to treat a variety of ailments. There is also a need for compositions and treatment methods that are useful with such devices. In addition, there is a need for a device that reduces the risk of the user being exposed to harmful amounts of radiation so that the device may be used safely without the supervision of a health professional.

SUMMARY OF THE INVENTION

According to one aspect of the invention, there is provided a therapy device for delivering electromagnetic radiation. The device comprises an energy source for emitting a desired wavelength of electromagnetic radiation and a proximity sensor for sensing proximity of the device to a desired surface the sensors can signal the energy source to activate or deactivate the emission of the electromagnetic radiation in accordance with the proximity to the surface.

The device can be used for a treatment of an ailment selected from the group consisting of arthritic pain, chronic pain, carpal tunnel syndrome, cellular damage, soft tissue injury, acne, TMJ, diabetic neuropathy, neuralgia, aging skin, seasonally affected disorder, inflammation, fine lines and wrinkles, mucositis, psoriasis, rosacia, eczema, oral candida, oral cancer, cellulitis, and wounds. The device can also be used for acne treatment and photorejuvenation therapy.

Another aspect of the invention provides for a faceplate for a therapy device comprising a substrate for supporting an energy source, a proximity sensor for sensing proximity of the faceplate to a desired surface, and a mount for attaching said substrate to a body. The body can be for housing a control mechanism for controlling said energy source. The sensor can send a signal to activate or deactivate said energy source in accordance with the proximity to the surface.

Another aspect of the invention provides for a method for controlling a therapy device having an energy source for emitting radiation, a proximity sensor for sensing proximity to a desired surface and a controller that is operably connected to the energy source. The method comprises the steps of:

receiving, at the controller, a signal from the proximity sensor in respect to the proximity of the device to the desired surface; and controlling the energy source in accordance with the signal from the proximity sensor.

BRIEF DESCRIPTION OF THE DRAWINGS

FIGS. 13A-13E show perspective sectional views of different embodiments of heads for a therapy device incorporating a proximity sensor in accordance with the present invention.

DETAILED DESCRIPTION OF THE INVENTION

Figure 1:
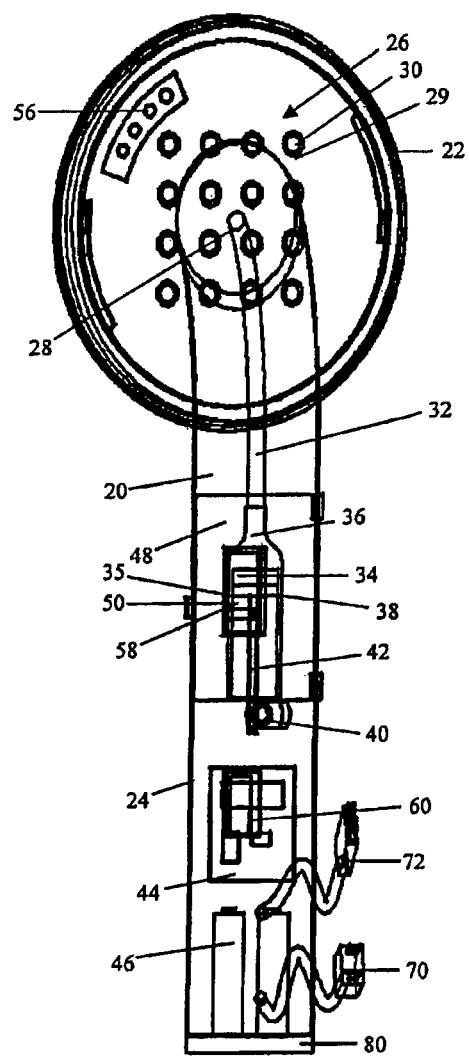
FIG. 1 shows a front phantom view of a device in accordance with one aspect of the present invention.

Disclosed and illustrated generally at 20 in the Figures is a hand held device in accordance with the present invention. The device includes a head 22 and a handle 24. The head 22 of the device includes a faceplate 23 and a baseplate 25. Faceplate 23 comprises an energy source 30, a substrate 57 for supporting energy source 30, and can have an outer surface 26. Substrate 57 and outer surface 26 each define at least one aperture 28 for allowing the distribution of a material 38 from the outer surface 26, as described further below. Substrate 57 can comprise a printed circuit board (PCB) or other structure functionally equivalent thereto. Outer surface 26 is comprised of a generally transparent material which allows maximal transmission of light from energy source 30 to the skin of the user during operation of device 20. Outer surface 26 can be manufactured from such suitable materials as glass, polycarbonate, Macrolon™, and the like. Outer surface 26 of faceplate 23 can further define apertures (not shown) for allowing light from energy sources 30 to be transmitted from outer surface 26. In an embodiment where such apertures are included, the transparency of outer surface 26 is not critical for allowing the transmission of light. Substrate 57 can also include an energy reflecting surface 27 designed to recycle energy reflected back from the user's skin when the device is in use by reflecting such energy back to the user's skin. The energy reflecting surface 27 can be located between energy source 30 and substrate 57 and can extend beyond the outer edges of energy source 30. Variations of energy reflecting layers may be used as known in the art.

It is also contemplated that device 20 can be used without outer surface 26. In such an embodiment, material 38 can be emitted directly from the at least one aperture 28 of substrate 57 or from at least one suitable extension (not shown) which extends from aperture 28 of substrate 57. In this embodiment, energy source 30 can be suitably protected, if necessary, from exposure to material 38 through means known in the art.

Faceplate 23 of the device can be of varied shape or design, as shown for example in FIGS. 10A to 10F. The handle 24 is designed to be easy to hold in one hand, and is connected to the head 22 through a flexible neck 68 or a fixed neck (not shown).

The size of the device should be suitable to allow the user to hold it in their hand during use. The faceplate should be of a size that is suitable to treat a portion of a person's skin and tissue.

The energy sources 30 can be of any type and of any wavelength that is suitable for the treatment at hand as known to persons skilled in the art. For example, energy sources 30 with a peak wavelength of about 415 nm and a bandwidth of about 20 nm can be used for the treatment of acne. The preferred embodiment of energy sources 30 for the present invention is one or more light emitting diodes (LEDs), however, the present invention is not limited to the use of these energy sources. Other energy sources including (without limitation) those that deliver microwave energy, radiofrequency energy, ultraviolet, visible, or infrared energy, ultrasound, laser energy, light energy or electrical stimulation, can also be used in place of or in combination with energy sources 30. Examples of known energy sources for delivering such energy include fluorescent lights, sulfur lamps, flash lamps, xenon lamps, LEDs, laser diodes, lasers, and filamentous lights. Examples of head 22 designs having varied energy sources are shown in FIGS. 10A, 10D, 10E and 10F, namely, a semiconductor energy source 31 such as an LED or a laser diode, a microwave energy source 33, a fluorescent tube 37, and a filamentous energy source 39.

The device 20 utilizes a power source, either internally housed (in the form of a battery 46) or external to the device (through a plug 70 for connecting the device in a standard electrical power receptacle), or both. The battery 46 can be disposable or rechargeable, can consist of one or more cells (for example, 2 cells as shown in FIG. 1) and can optionally be accessed for removal from the device by removing battery cover 80.

Housed within the handle 24 is a controller 34, which preferably is activated with a switch 35, through which the user controls the device. The controller 34 allows the user to "turn on" and "turn off" the device, though the turning off of the device can be done automatically by the device at the appropriate end of treatment, as described below. The user can turn on and use the device for a predetermined amount of time based on instructions for a treatment regimen that accompany the device or instructions prescribed by a medical professional. The instructions can be in written, audio, or video form, or can be downloaded from a computing device or computer network. Optionally, the controller 34 can also be used to select a treatment regimen, though this can also be done automatically through the use of coded containers or face plates, as described below.

The handle 24 also houses a processor 44, which can be pre-programmed with suitable treatment regimens. The processor 44 is used to time the duration of treatment, or to pulse or otherwise modify the energy source 30 to optimize the treatment. For example, for the treatment of acne, the user might set the controller 34 to an acne treatment setting (or to an 'on' position if the treatment setting is automated as described below) and then place the device proximal to the skin being treated, and would activate the device through the controller 34. The processor 44 can control or vary the duration, intensity, and pulses of energy being administered to the patient in accordance with the treatment, and can also signal the patient through an audible tone or other method, when the treatment is finished. The processor 44 can also act as a controller for the dispensing of appropriate amounts of material 38 at appropriate times, as further described below.

The head 22 of the device 20 includes a faceplate 23 that can be removed by the user from a baseplate 25 through means such as a bayonet mount 54 or other suitable mounting means, for example, through mechanical fittings. Thus the same device 20 can be fitted with various faceplates 23, each with different energy sources or other operational or structural features. Information can be transferred from the faceplate 23 to the device 20 for use by the processor 44 by a connector 56 disposed on faceplate 23, which is connected to connector 52 disposed on baseplate 25 Connector 52 communicates with processor 44 via cable 86 indicating which faceplate 23 is connected to the device, allowing the processor 44 to identify the treatment regimen that corresponds to the particular faceplate 23. Moreover, in this embodiment, power transmission from device 20 to faceplate 23 and data communication between processor 44 and faceplate 23, when faceplate 23 contains memory, is also accomplished through the connection established between connectors 52 and 56. However, in other embodiments, identification information, power transmission and data communication between any memory present on faceplate 23 and processor 44 can be accomplished using different types of mechanisms and connections. For example, separate pairs of connectors can be used for the transmission of power, communication of identification information and data communication. Alternatively, other connection types can be used for data communications between faceplate 23 and device 20, such as a wireless connection based on radio transmission. Moreover, the identity of a faceplate 23 can be contained on faceplate 23 as an identifier readable by a sensor located on device 20. In yet other embodiments, other methods for identifying the faceplate may be used. An electrical coding can be set into faceplate 23 using alternating bands of conducting and non-conducting material can be read by faceplate sensors located on device 20. Alternate mechanisms of communicating identity information can also be used, such as a bar code and optical sensor system, a magnetic strip and magnetic strip reader, an electrical contact, or a mechanical key recognition system. These and other such variations are within the scope of the invention.

The use of a variety of interchangeable faceplates 23 permits the user to purchase a low cost device that is optimized for the ailment to be presently treated, while allowing the user the flexibility to expand treatment options in the future by purchasing a new faceplate 23, rather than a whole new device. Interchangeable faceplates 23 have the added benefit that they can be easily removed from the device 20 for washing or autoclaving. Alternatively, if costs permit, the device can be manufactured with one form of integrally or permanently attached faceplate only and additional units for other treatments can similarly be manufactured.

A simpler form of therapy device comprising a body, an energy source disposed on the body for emitting a desired wavelength of electromagnetic radiation, preferably light radiation, and a material dispensing system disposed on the body for dispensing a desired material for use with the device, falls within the scope of this invention. This device can operate under manual control, where the user determines the duration and frequency of treatment.

The therapy device can be sold as a kit comprising the assembled device together with instructions for usage and possible treatment regimens or protocols. The instructions can be in written, audio, or video form, or can be downloaded from a computing device or computer network. The instructions can be provided by a medical professional. The therapy device can be sold unassembled as part of a kit, in which case the kit can further comprise instructions for assembly of the device.

Figure 11:
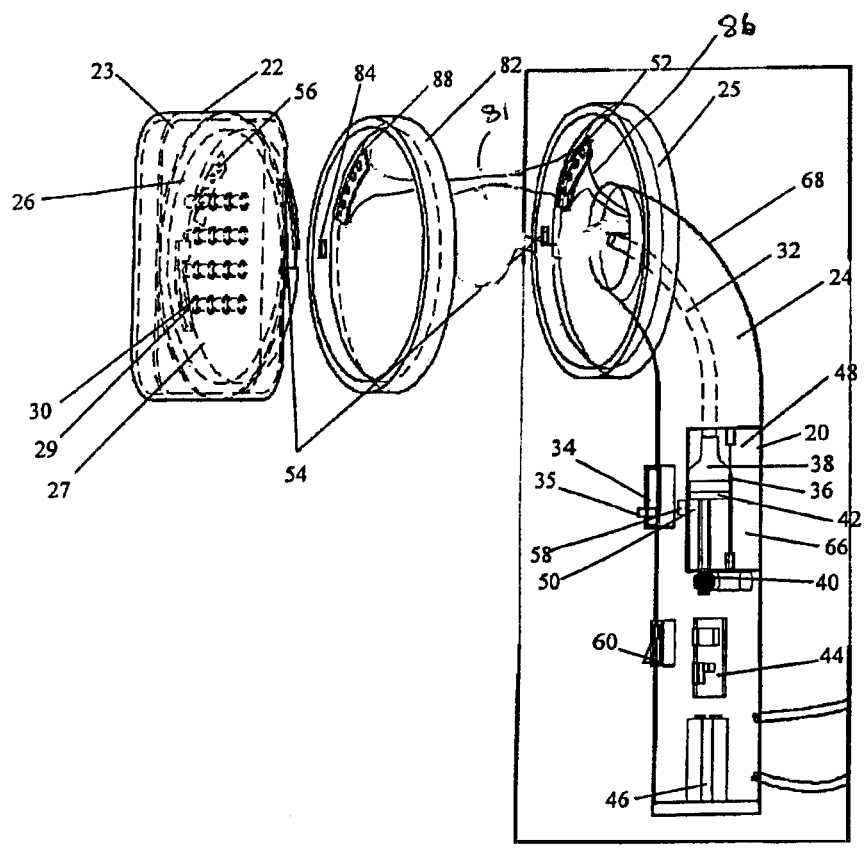
FIG. 11 shows an exploded side phantom view of the device of FIG. 1 fitted with an adapter in accordance with a further aspect of the present invention.

The device can also include an adapter 82 for receiving faceplate 23 and facilitating the use of the device over treatments when it can become uncomfortable to hold the entire device with the handle over time. The adapter 82, shown fitted to the device in FIG. 11, contains faceplate attachment means 84, which are compatible with and complementary to the bayonnet mount 54, and an extension cable 81 running from the faceplate attachment means to the baseplate 25 and functionally connected thereto. Extension cable 81 would allow the powering of the energy source 30 on faceplate 23 by the battery 46 and processor 44 on the handle 24 through the extension cable 86. The adapter 82 can also contain adapter connector 88 for the remitting of faceplate information to processor 44, also through the extension cable 86 which can be connected to the connector 52 or the baseplate 25 to facilitate such remitting of information. The adaptor 82 can also contain straps for affixing faceplate 23 (connected to adaptor 82) to the user during treatment (not shown).

Figure 5:
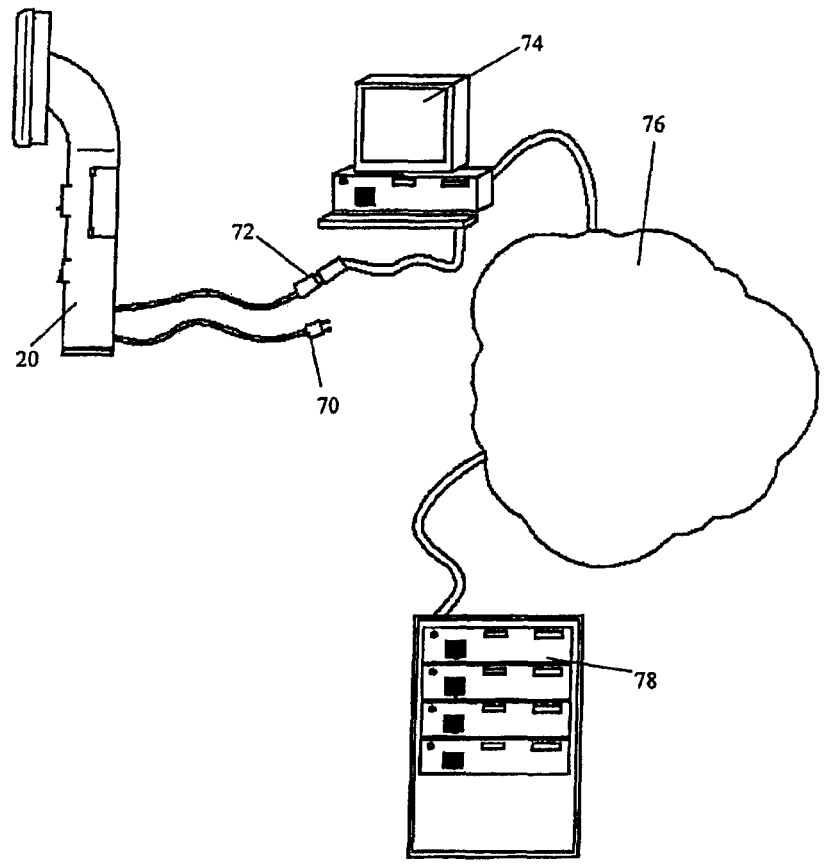
FIG. 5 shows a device connected to a database server through the internet in accordance with another aspect of the present invention.

The device 20 can also provide for updating the software of the processor 44 as new faceplates 23 or new treatment regimens are designed. Referring to FIG. 5, processor 44 can connect by wire connection through firewire 70 or by Universal Serial Bus 72, as shown, or through another wired or wireless communication means such as an Infrared port (not shown) to a personal computer 74 connected through the Internet 76 to a database server 78 containing an updated database of treatment regimens. Such communication can also occur through a wireless local area network, bluetooth, or other communications technology (not shown) or through the insertion of a flash card or other memory-containing device which contains pre-programmed instructions or data (not shown). Updating of the device can be passive (occurring in real-time as new software is developed) or active, occurring only at the request or command of the user. Alternatively, the device can be pre-programmed with treatment protocols and can not have software updating means.

Although faceplate 23 of device 20 can be interchanged with other faceplates 23 to optimize the treatment regimen for a variety of ailments, it is possible that a single faceplate 23 would contain a suitable energy source 30 for a broad subset of ailments. For example, faceplate 23 can include an energy source comprised of LEDs for emitting electromagnetic radiation at about 410 nm and other LEDs for emitting electromagnetic radiation at about 630 nm. Other medically useful electromagnetic emissions occur at about, for example, 580 nm, 660 nm, 680 nm, 800 nm, 810 nm, 820 nm, 830 nm, 840 nm, and 900 nm, with a band width of about 40 nm, more preferably about 20 nm. Alternatively, faceplate 23 can include an energy source comprised of LEDs, Xenon light source, arc-lamps or other energy sources for emitting electromagnetic radiation at about 360 to 380 nm. Therefore, depending on the flexibility of head design, it can be necessary to have a secondary way in which to select treatment regimens. For example, the controller 34 can include a user interface (not shown) to allow the user to program or select various treatment regimens by hand. Optionally, an automated mechanism for the determination of treatment regimens is possible, such as by using coded, treatment-specific containers, as described below.

The device preferably also includes a system for dispensing a desired material 38 such as a gel or lotion for use in the treatment. During treatment using device 20, material 38 is disposed between the skin of the user and faceplate 23. Material 38 can optimize and/or enhance the energy transfer between energy source 30 and the skin of the user by filling in irregular voids that exist on the surface of the skin. Another function of material 38 can be to alter the refractive index of the skin or target tissue so that the absorption spectrum of the skin or target tissue is closer to the emissions spectrum of the source of electromagnetic radiation. This aspect of material 38 can be useful because the skin has an index of refraction of about 1.4 in the visible and the near infrared, which is larger than that of air. As a result, any photon that interacts with the air-skin interface is deflected if it does not hit the skin at an incidence angle of substantially 0°. Since the surface of the skin is irregular, the angular distribution of the skin increases. In order to enhance the absorption of light into the skin, material 38 can comprise components that have an index of refraction which is close to that of skin. Such components are sometimes called skin index matching materials. An example of a suitable index matching material is propylene glycol solution with a refractive index of 1.5. Material 38 can thereby enhance the absorption by the user's skin of photons emitted by energy source 30 by improving the surface irregularities of the skin and minimizing the difference of the indices of refraction between the skin and the area between the skin and the faceplate 23. Material 38 can also act as a lubricant or hydration agent that provides a low friction surface coating for improving the comfort and operation of the device. For example, material 38 can comprise a gel, such as a water based gel. Material 38 should be transparent to the beneficial light emitted by energy source 30. In a preferred embodiment of the present invention, outer surface 26 of device 20 is pressed or placed against with the surface of the user's skin thereby causing the surface of the skin to be substantially contiguous with outer surface 26, and material 38 is disposed therebetween during treatment with device 20.

Material 38 can also contain a medicament, active ingredient, or supplement known to be useful in treatment of a specific indication. For example, the material 38 can contain an acne treatment such as benzoyl peroxide, preferably in a concentration of about 0.1% to 10%. This allows the user to combine a treatment using electromagnetic radiation with a more conventional treatment for their ailment using minimal steps. The material can also contain ingredients such as aloe, Vitamin E, a hydration agent, Vitamin C, Vitamin D, Vitamin A, Vitamin K, Vitamin F, Retin A (Tretinoin), Adapalene, Retinol, Hydroquinone, Kojic acid, a growth factor, echinacea, lanolin, an antibiotic, an antifungal, an antiviral, neutraceuticals, cosmeceuticals, a bleaching agent, an alpha hydroxy acid, a beta hydroxy acid, salicylic acid, antioxidant triad compound, a seaweed derivative, a salt water derivative, algae, an antioxidant, a phytoanthocyanin, phthalocyanine, a phytonutrient, plankton, a botanical product, a herbaceous product, a hormone, an enzyme, a mineral, a genetically engineered substance, a cofactor, a catalyst, an antiaging substance, insulin, trace elements (including ionic calcium, magnesium, etc.), minerals, minoxidil, a dye, a natural or synthetic melanin, a metalloproteinase inhibitor, proline, hydroxyproline, an anesthetic substance, benzoyl peroxide, amino levulinic acid, chlorophyll, bacteriachlorophyll, Coenzyme Q10, copper chlorophyllin, chloroplasts, carotenoids, phycobilin, rhodopsin, anthocyanin, and derivatives, subcomponents, immunological complexes and antibodies directed towards any component of the target skin structure or apparatus, and analogs of the above items both synthetic and natural, as well as combinations thereof. It will be noted by those skilled in the art that the medicaments, active ingredients, and/or supplements disclosed herein and their equivalents, as well as any other medicaments, active ingredients, and/or supplements that can be useful when used in combination with the device and methods of the present invention, can also have index matching and skin smoothing properties that can contribute to the effectiveness of the treatment.

The medicament, active ingredient, or supplement can be photosensitive and can undergo a photochemical reaction when applied to the skin and exposed to energy source 30.

The medicament, active ingredient, or supplement can be administered to the skin or target tissue before use and separately from administration of material 38 and use of device 20.

Figure 2:
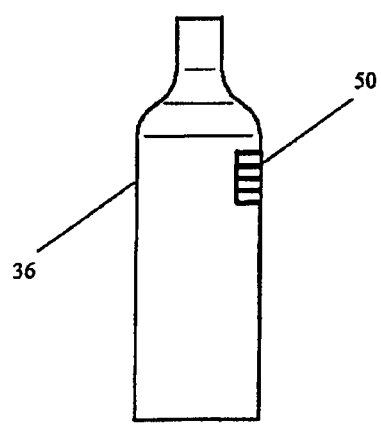
FIG. 2 shows a front view of a removable container used in the device of FIG. 1.
Figure 3:
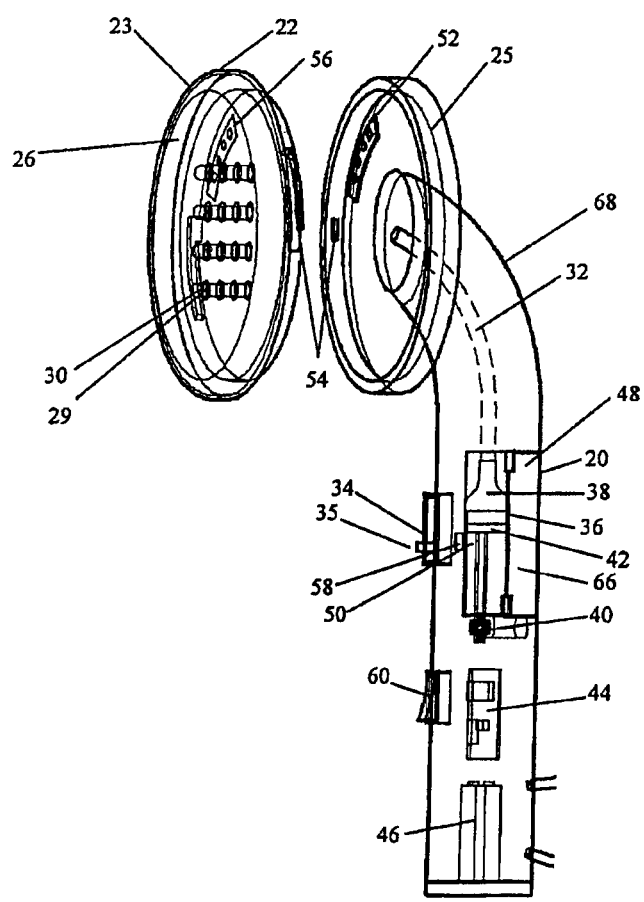
FIG. 3 shows an exploded side phantom view of the device of FIG. 1.
Figure 4:
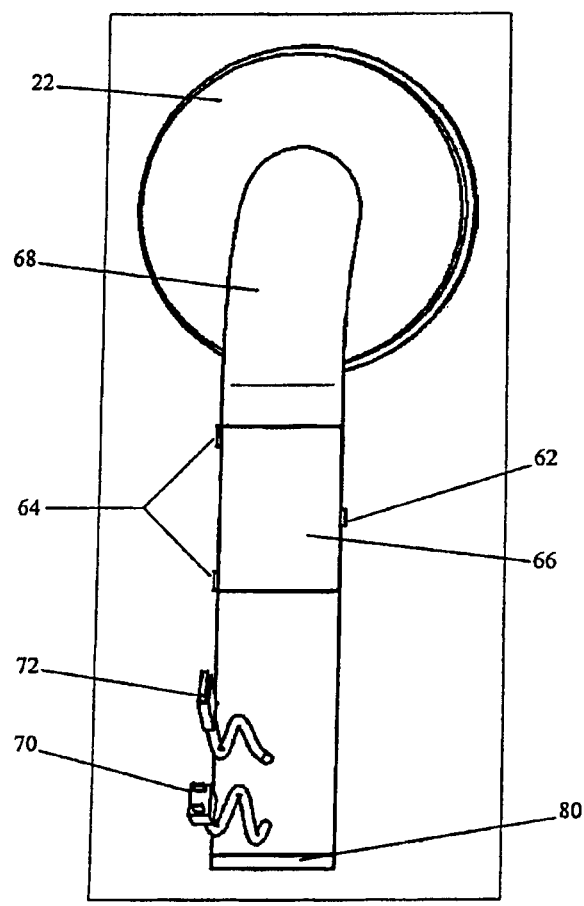
FIG. 4 shows a back view of the device of FIG. 1.

A removable container 36, shown in isolation in FIG. 2, containing material 38, as described above, is housed within a container receiver 48, such as a cavity or slot within the device, preferably located on the device handle and preferably having a door 66 that is retractable or that is rotatably mounted on hinges 64 and lockable in a closed position using latch 62, or a similarly re-sealable opening for insertion and removal of the container. The container can be disposable, or can be refillable. The container can also be filled by a dermatologist, pharmacist, or other medical professional, for prescription dispensing or customizable formulations of material.

The material 38 is squeezed out of the container either manually by the user using, for example, a spring-loaded trigger mechanism 60 operably connected to a plunger 42 or other squeezing mechanism or pump mechanism for displacing material 38 out of the container 36, or automatically and under processor 44 control when the device is activated, using, for example, an electric motor 40 or solenoid (not shown) operably connected to a plunger 42 or other squeezing mechanism for displacing material 38 out of the container 36, and a motor control system for turning on and off the motor (as shown, incorporated within processor 44). As would be recognized by those skilled in the art, other suitable pumping or dispensing mechanisms could be used, such as a diaphragm pump, which would also aid in dispensing a predetermined amount of material 38 during operation of device 20.

The material 38 displaced out of the container 36 is forced through one or more apertures 28 on the device head 22, either directly (not shown) or through one or more distribution passages 32 built into the device and connecting the container 36 to the apertures 28. In this manner, the appropriate amount of material 38 is distributed directly to the space between the skin of the patient (not shown) and faceplate 23 with little effort from the user.

In order to make the therapy easy to administer, the container 36 can be clearly labeled for the ailment it is meant to treat, as well as with its ingredients. Various materials can therefore be prepared and sold separately, in containers compatible with the device, for repeat applications of a wide variety of treatments for a wide variety of ailments.

In order to simplify the use of the device, individual containers 36 can be designed to communicate with the device. For example, an electrical coding 50 set into the container 36 using alternating bands of conducting and non-conducting material can be read by container coding sensors 58 on the device 20. Alternate communication means can also be used, such as a bar code and optical sensor system (not shown), a magnetic strip and magnetic strip reader (not shown), an electrical contact (not shown), or a mechanical key recognition system (not shown).

In this manner, the device can determine which treatment is to be performed based on which container 36 is in the device. The processor 44 can determine the appropriate rate and amount of material 38 to be displaced from the device 20 during treatment, based on the type of material 38 in the device as read by the sensors 58 from the data on the container's electrical coding 50. In this way, the processor 44 acts as a form of "motor control system" for the dispensing of the material.

The processor 44 can also determine whether the appropriate faceplate 23 is on the device for the treatment required (based on the type of material that is loaded in the device), and can activate the energy sources 30 for the appropriate treatment regimen (again, based on the type of material 38 that is loaded in the device 20). For example, when an "acne" material 38 is loaded into the device 20, the processor 44 "reads" the type of material loaded using container coding sensors 58, accesses its internal database to determine what the appropriate treatment regimen is for acne (including type, duration and intensity of energy emission, (for example, an 18 minute treatment with combination 620 nm and 415 nm LEDs with a total energy output of 40-90 joules (J) per session in a continuous wave)) as well as what is the appropriate timing, rate, and amount of material to be dispensed.

Figure 6:
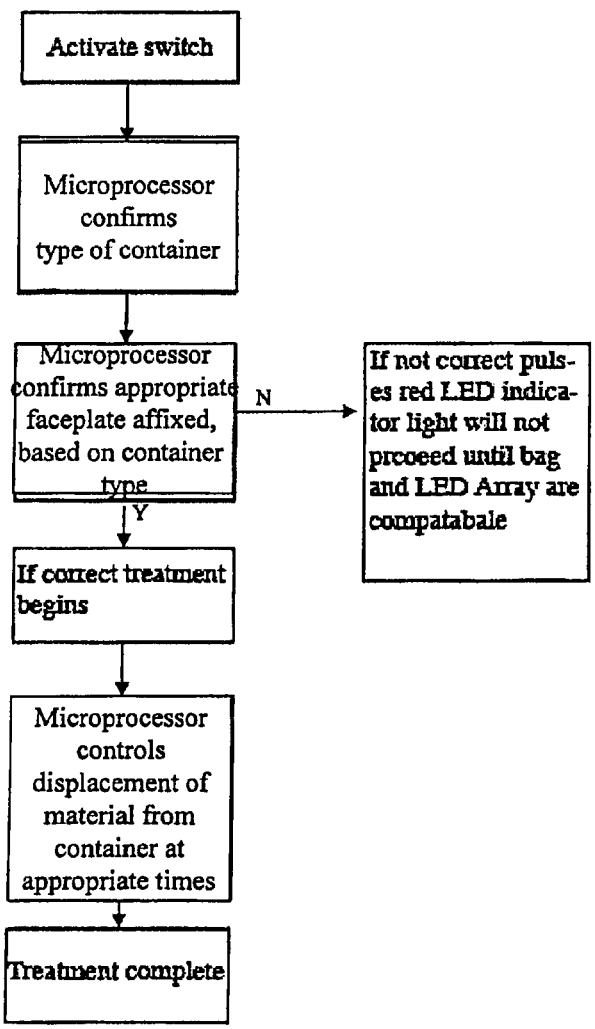
FIG. 6 shows a computer flow chart detailing processor steps for the device of FIG. 1.

A flow chart showing generally an example of how the processor 44 can process information from the container 36 and the faceplate 23 is shown in FIG. 6.

The processor 44 verifies that the correct faceplate 23 is on the device by communicating with faceplate 23 through connectors 52 and 56 (to ensure, for example, that a faceplate 23 with light sources 30 capable of emitting light at 415 nm is affixed to the device). The device will activate when the controller 34 is deployed, and when the appropriate faceplate 23 and container 36 are affixed to the device. Optionally, the device can also use a counter, sensors or other means, typically affixed to the plunger 42, to determine whether there is enough material 38 in the container 36 to undergo the appropriate treatment regimen, and will warn the user if the amount of material is insufficient, or if the container is nearly empty.

Figure 7:
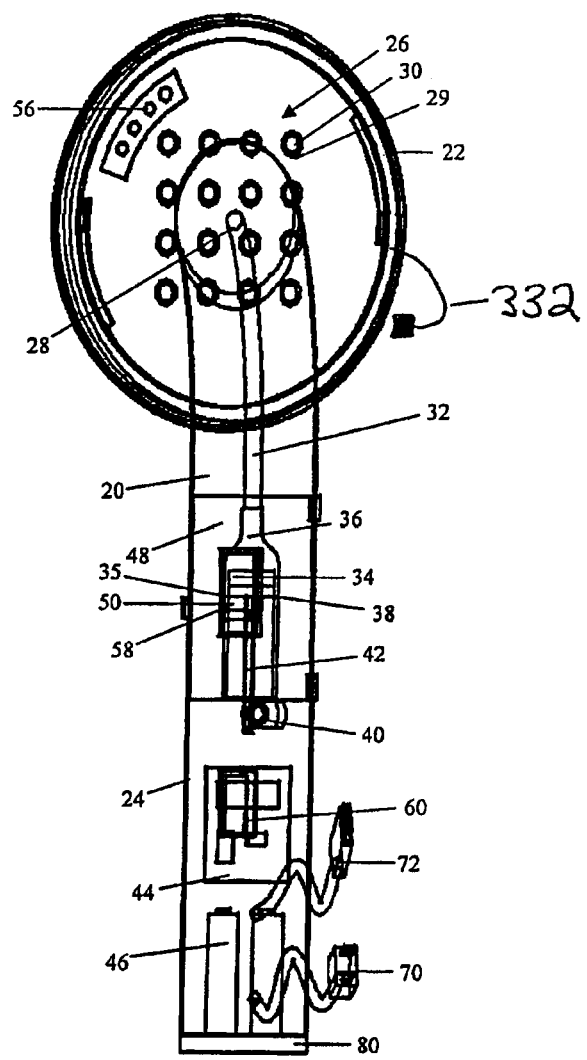
FIG. 7 is a cross-sectional view of the device shown in FIG. 1 and shows a temperature sensing device in accordance with one aspect of the present invention.

Optionally, device 20 can further comprise a temperature sensing device such as temperature sensing device 332 shown, for example, in FIG. 7, for measuring the temperature and/or any change in temperature at the skin-device interface. Temperature sensing device 332 comprises a thermal conductive material 51, such as copper metal or other thermal interface material, and a thermal transducer 53, such as a p-n junction diode or thermistor. Thermal conductive material 51 extends from outer surface 26 and is in communication with thermal transducer 53. Thermal transducer 53 is in communication with processor 44. It will be understood by those with skill in the art that other devices which incorporate the functions of temperature sensing device 332 would be suitable. For example, a temperature sensing device which is flush with at least part of the face plate that contacts the user's face during use is contemplated.

It will be recognized by those with skill in the art that the configuration of energy source 30, and temperature sensing device 332 (if used) can be implemented on a PCB or other structures functionally equivalent thereto.

Figure 8:
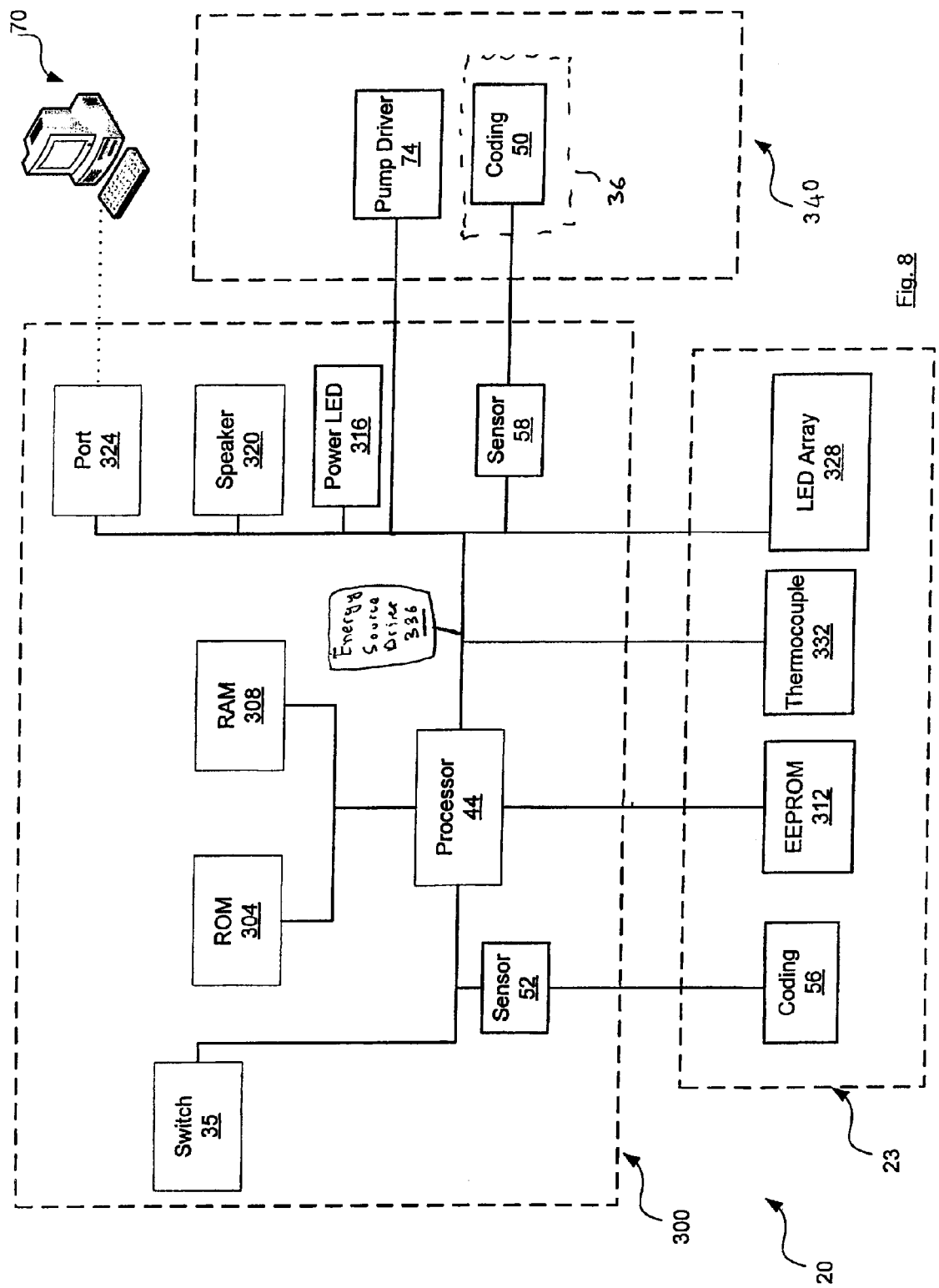
FIG. 8 is a block diagram showing electronic components in accordance with one aspect of the present invention.

Referring now to FIG. 8, a block diagram of certain components of device 20 are shown according to an embodiment of the invention. In this embodiment, device 20 includes a control mechanism 300, a faceplate 23 and a dispensing system 340.

Control mechanism 300 has a processor 44. Processor 44 is connected to a persistent storage device which, in this embodiment, is a flash memory 304 containing a plurality of applications executable by processor 44, and related data that enables device 20 to perform certain functions. Processor 44 is also connected to a random access memory unit ("RAM") 308. Processor 44 can send output signals to various output devices including alarm sources which in this embodiment are an LED 316, and a speaker 320. Processor 44 can also receive input from various input devices including switch 35 and sensor 52.

Control mechanism 300 also includes an energy source driver 336. Energy source driver 336 is operable, through a control signal from processor 44, to deliver a driving current to the energy source located on faceplate 23. Both processor 44 and driver 336 are also connected to connector 52. In this embodiment, connector 52 is a five pin surface mount connector.

Control mechanism 300 is operable to communicate with faceplate 23 through connector 52. Faceplate 23 includes an energy source, which in this embodiment is an LED array 328, an electrically erasable programmable read only memory (EEPROM) 312 and a temperature sensing device 332, all of which are in communication with control mechanism 300 through connector 56 which connects to connector 52.

In a preferred embodiment, LED array 328 contains thirty six LEDs, each LED capable of generating about 12 mW of power at about 100% duty cycle under continuous operation at a current of about 25 mA, which current is supplied by energy source driver 336 through connectors 52 and 56. In other embodiments, other types of LEDs with different operational characteristics can be used and these embodiments are within the scope of the invention.

EEPROM 312, in this embodiment, is a 1-wire EEPROM as, for example, manufactured by Maxim Integrated Products, Inc. of California U.S.A. Temperature sensing device 332, in this embodiment, is a solid state temperature sensing device such as MCP9700, a low-power voltage output temperature sensor, manufactured by Microchip Technology Incorporated of Chandler, Ariz., U.S.A.

EEPROM 312 is responsible for storing additional data relevant to the performance of certain functions. This data is accessible by processor 44 through connector 52. As now apparent to those skilled in the art, in other embodiments, other persistent storage devices such as a ROM or flash-memory can be used in place of an EEPROM for storing the additional data on face place 23 and these embodiments are within the scope of the invention. Temperature sensing device 332 detects the temperature at the interface of faceplate 23 and the skin and is operable to convey this temperature reading to processor 44. LED array 328 is operable to deliver an energy according to a current supplied by energy source driver 336.

Control mechanism 300 is also operable to communicate with dispensing system 340. Dispensing system 340 includes a pump driver 74 and a coding 50 which is located on container 36. Driver 74 is operable, through a control signal from control mechanism 300, to drive a solenoid to deliver a predetermined amount of fluid contained within container 36. In this embodiment, container 36 is a container for delivering benzoyl peroxide with a concentration of 2% which is delivered from container 36 to the skin by a series of pumps or pulses actuated by driver 74. Coding 50, as previously described, is formed from alternating bands of conducting and non-conducting material. The coding combination allows a different voltage to be returned to processor 44 corresponding to different container types. As it is now apparent to those skilled in the art, in other embodiments, other coding mechanisms can be used such as different resistors Processor 44 is also operable to communicate with a computing device 70 through an interface operable to conduct communications when a computing device 70 is optionally connected to the interface. In this embodiment, the interface is the communications port 324 which uses communications protocol RS-232 known to those skilled in the art, and hence is a serial port. As it is now apparent to those skilled in the art, in other embodiments, other types of communication protocols or interfaces can be used for connecting to a computer. These interfaces include but are not limited to Universal Serial Bus (USB), infrared (IR), Blue Tooth, two-way radio, wired Ethernet and wireless Ethernet connection using a variety of protocols such as 801.11g or 801.11b. Moreover, the type of computing device that can be connected to device 20 includes, but is not limited to, a desktop personal computer (PC), a laptop, a personal digital assistant (PDA) or any other mobile or stationary device that is capable of communicating, processing and storing information.

Control mechanism 300 maintains a treatment database 200, used for determining different parameters of a treatment regimen. Database 200 contains information relevant to treatment 10 regimens such as the duration of a specific treatment and duration and intensity of energy delivered during a cycle. Accordingly, a separate database record exists for each different treatment regimen. Typically, records are stored in database 200, which is maintained in flash-memory 304. However, some records, or portions thereof, can also be stored in EEPROM 312 located in faceplate 23. The records or portions thereof that are maintained in EEPROM 312 contain information that is specific to 15 the treatment regimen or regimens that are deliverable using that particular faceplate 23. Table I shows an example record 204, labeled Record #1 that contains data for an example acne treatment regimen and is maintained in EEPROM 312.

TABLE I

Example record 204 for an example acne treatment regimen
Record #1

| | Field Type | Value |
|---|---|---|
| Field 1 | Treatment type | Acne |
| Field 2 | Initial Duration of each cycle | 90 seconds |
| Field 3 | LED Efficiency | 12 mW/25 mA |
| Field 4 | Form of Activation | 40 |
| Field 5 | Target power delivery per cycle | 30 J |
| Field 6 | Upper heat limit | 41° C. |
| Field 7 | Lower heat limit | 35° C. |
| Field 8 | Number of pump pulses | 3 |
| Field 9 | Container type | 5 |
| Field 10 | Energy Source | LED array |

Describing Table I in greater detail, Field 1 contains the type of treatment regimen contained in this record which in this example is a regimen for Acne. Field 2 contains the initial duration of each treatment cycle, while Field 3 contains the operating efficiency of LEDs found in LED array 328. These fields are set to about ninety seconds and about 12/25 mW/mA respectively for this example regimen. Field 4 contains the form of activation for LED array 328. In this embodiment, two forms of activation are possible. The first is continuous wave where LED array 328 is activated continuously, and the second is pulse wave, where LED array 328 is activated in pulses. In this example, Field 4 is set to 40 meaning that during a cycle, LED array 328 is to be activated at a pulse rate of about forty Hertz.

Activating LED array 328 at a certain current for a specified period of time results in a certain amount of irradiance power being delivered by LED array 328. Accordingly, the irradiance power to be delivered during a cycle is the amount of power generated corresponding to the time, current and form of activation of LED array 328 specified in Fields 2 through 4 and is based on the efficiency of LEDs used (which is specified in Field 3). This power, referred to as target cycle power, is specified in Field 5. In this example, it is targeted that a combination of LEDs used should result in the delivery of about thirty Joules by LED array 328 when LED array 328 is activated at about a forty Hz pulse for a ninety second period. Accordingly, in this example, Field 5 is set to about thirty Joules.

Continuing with the description of Table I, Fields 6 and 7 specify temperature limits within which device 20 is to keep the temperature of faceplate 23 during the treatment. In this example, the temperature is maintained between about thirty-five and about forty-one degrees centigrade. Field 8, contains the number of times container 36 is to be pumped prior to the activation of LED array 328. This field, in effect, determines the amount of fluid to be delivered by container 36 during a treatment. In this example, container 36 is to be pumped 3 times. Field 9 specifies the type of container this regimen will work. In this case, the container with a code of 5 is the appropriate container to be used. In other embodiments, multiple container types can be deemed compatible with a treatment regimen and such embodiments are within the scope of the invention. Field 10 specifies the type of energy source present on the corresponding faceplate. In this example a 415 nm LED array is used.

Control mechanism 300 also maintains several variables such as a power down timer 208 used for counting down to the point where device 20 is to enter a low power mode, in effect shutting it down. A treatment timer 212 and a power counter 216 are also maintained to track the amount of time and power that has been delivered in a given cycle. Control mechanism 300 also maintains logging data which contains information about the usage of device 20, that can be used in making determinations about the efficacy of the treatments used and the maintenance of device 20. For example, logging data can comprise logging variables that include counters for counting the duration that LED array 328 has been activated, causing an alarm to be delivered if LED array 328 have been used for ninety percent of their useful life, reminding the user to replace the faceplate. In another example, a doctor could monitor a patient's use of the device by examining the logging variable that tracks how long device 20 has been used since a particular date. The device can be disabled after it has reached the end of its useful life cycle, for example, after 2000 hours. In this embodiment logging data are maintained in flash memory 304. In other embodiments, logging data could be maintained in a separate storage device dedicated to storing these variables such as an additional flash-memory unit or an EEMPROM. These and other variations are within the scope of the invention.

Figure 9:
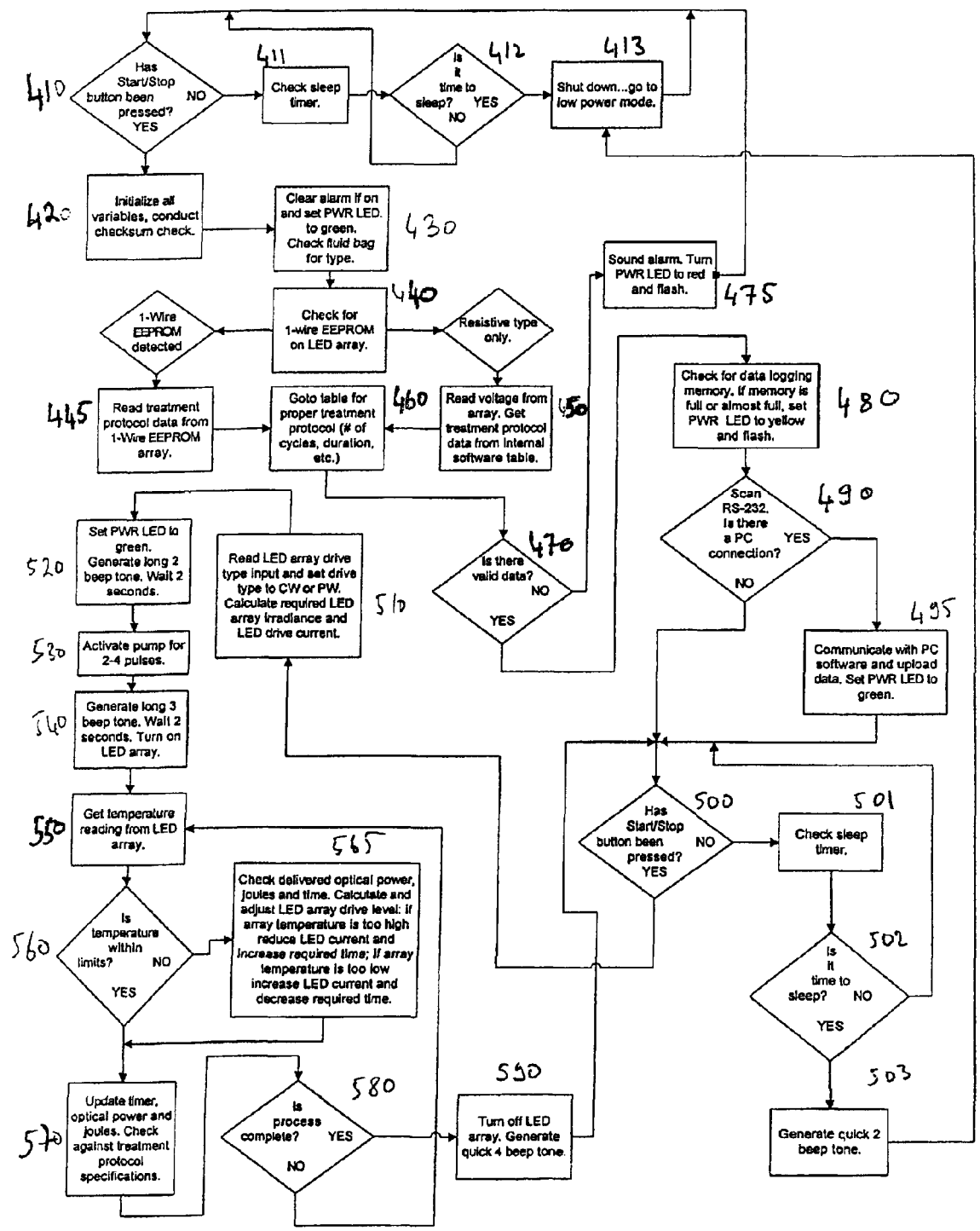
FIG. 9 is a flow chart showing a method in accordance with one aspect of the present invention.
Figure 10:
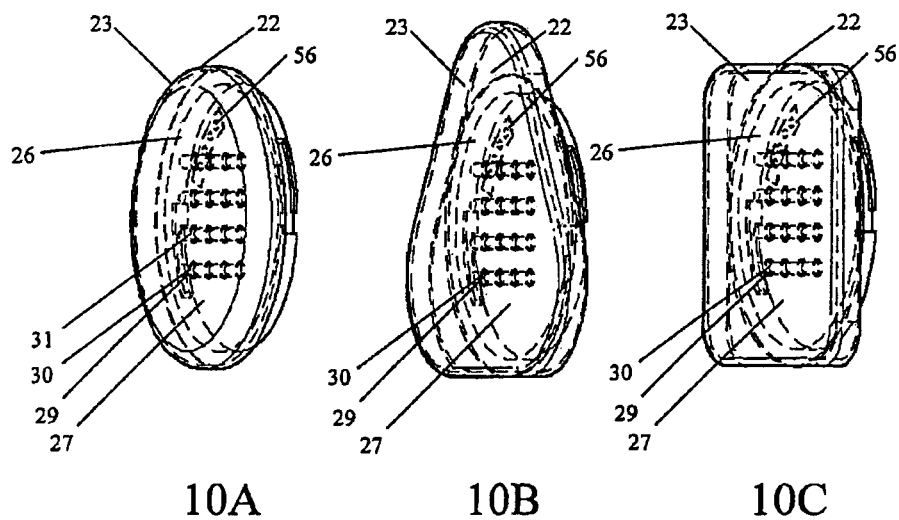
FIGS. 10A-10F show side phantom views of various head designs for the device of FIG. 1.
Figure 10:
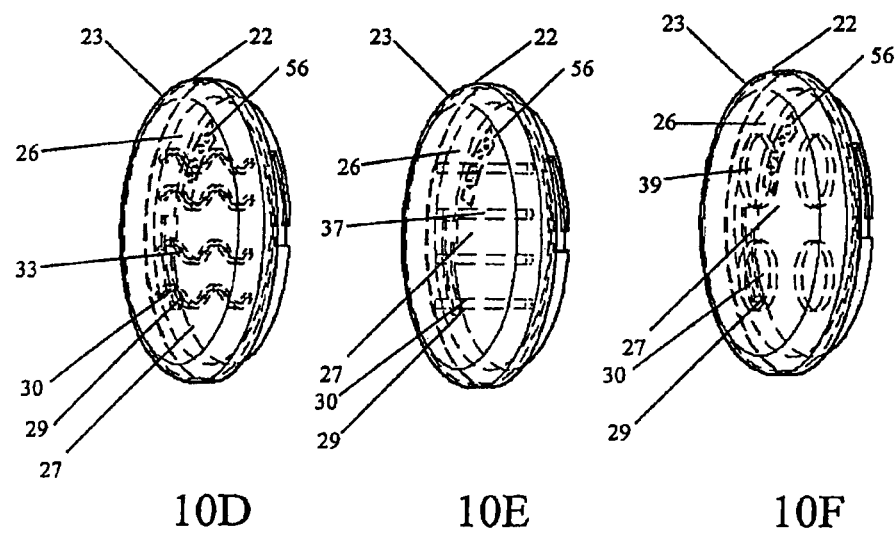

Referring to FIG. 9, a method for delivering a treatment regimen is indicated generally at 400. In order to assist in the explanation of the method, it will be assumed that method 400 is performed using device 20. Furthermore, the following discussion of method 400 will lead to a further understanding of device 20 and its various components. (However, it is to be understood that device 20 and/or method 400 can be varied, and need not work exactly as discussed herein in conjunction with each other, and that such variations are within the scope of the invention).

The current performance of method 400 is initiated by pressing switch 35 to turn the device on while device 20 is in a low power mode. Referring to FIG. 9, at step 410, a determination is made whether switch 35 has been pressed. While in low power mode, device 20 loops through step 410 continuously. Hence, when switch 35 is pressed, the determination is made that switch 35 was pressed, and, accordingly, method 400 advances to step 420.

At step 420, device 20 is initialized. In this example, variables maintained by device 20 are set up in RAM 308 and initialized. For example, timer variable 208 that counts down to a time when device 20 is to enter a low power mode is set to 300, meaning that 300 seconds remains to power down. The value of power down timer 208 is decremented in the background throughout the performance of method 400. Treatment timer 212 and power counter 216 are set to zero since the treatment has not started at this point. In addition, logging variables are also moved to RAM 308 and initialized with the values currently stored in flash memory 304 so that they can be updated, as appropriate, during this activation of device 20. Moreover, a checksum of flash memory 304 is performed in the usual manner to check for proper operation.

Moving to step 430, the type of container 36 present in device 20 is determined. In this embodiment, step 430 is performed by having processor 44 read the electrical coding 50 set into container 36 through sensors 58. In this example, it will be assumed that container 36 is filled with benzoyl peroxide with a concentration of 5% and that the container code is 5. Also, at this step, power LED 316 is set to green indicating normal operation of the unit. Furthermore, any output to speaker 320 is discontinued to turn off any ongoing alarms.

Continuing with the performance of method 400, at step 440, a determination is made as to the type of faceplate 23 that is present on device 20. This is accomplished by having processor 44 detect the presence of an EEPROM, through connector 52, using a presence pulse or other suitable known methods. In this example, as discussed above, it is assumed that faceplate 23 does contain an EEPROM 312. Accordingly, step 460 is performed.

At step 460, treatment regimen data is retrieved. In this example, record 204 is retrieved by processor 44, from EEPROM 312. Specifically, processor 44 moves the record 204 to RAM 308 for use during the delivery of the treatment. In other embodiments where faceplate 23 can be used with more than one treatment regimen, the user can be presented with a selection of regimens available and asked to pick the one to be used. Subsequently, the record associated with the selected regimen would be retrieved. For example, the selection can be made by pressing switch 35 a prescribed number of times. These and other such embodiments are within the scope of the invention.

At step 470, the contents of record 204 are validated. In this embodiment, the validation is performed by ensuring that the fields of record 204 are not blank. In other embodiments, other methods of data validation can be used. For example, a separate database could be maintained in ROM 304 or EEPROM 312 specifying valid ranges of values for the fields of a record. Each record can then be validated against this second database. In this example, it is assumed that the record 204 contains valid data. As part of the validation step, the type of container detected at step 430 is compared to Field 9 of record 204 which specifies compatible containers. In this example, Field 9 has a value of five which is the container code detected at step 430. Accordingly, container 36 is deemed compatible with faceplate 23.

Continuing with the performance of method 400, at step 480, the capacity of RAM 308 is determined. If RAM 308 is full, namely no free memory remains to be used during the delivery of the treatment regimen, processor 44 generates an alarm by sending a signal to power LED 316 causing it to turn yellow and flash. In this example, it is assumed that there is memory remaining for use, and hence, no alarm is generated. As it is now apparent to those skilled in the art, different criteria can be used in determining the capacity of RAM 304. For example, in other embodiments, an alarm can be generated if greater than a certain percentage, such as greater than ninety five percent, of RAM 304 is occupied. These and other variations are within the scope of the invention.

At step 490, the presence of a connection to a local computer is detected. In this embodiment, processor 44 determines, in the usual manner, whether a computing device 74 is attached to the RS-232 port of device 20. In the present embodiment it is assumed that a device is attached. Accordingly, step 495 is performed.

At step 495, logging data are uploaded to computing device 74, freeing the corresponding space in flash memory 304. In this example, processor 44 removes the logging data from flash memory 304, and transfers it to computing device 74 through port 324. In other embodiments, other events in addition to the detection of computing device can be added to initiate uploading of logging data to computing device 74. For example, a user at computing device 74 can be asked to initiate uploading by providing a command such as a mouse click, at computing device 74. Alternatively, device 20 can deliver an alarm to the user when the presence of computing device 74 is detected and wait for a response from the user in the form of pressing switch 35. These and other such embodiments are within the scope of the invention.

At step 500 a determination is made whether switch 35 has been pressed. Pressing switch 35 allows the treatment to begin. Otherwise, method 400 loops through step 500 until switch 35 is pressed. In this example, it is assumed that switch 35 is pressed, indicating that the treatment is to begin.

Continuing with method 400, at step 510, the properties of irradiance to be delivered is determined. To determine the properties of irradiance, the type of energy source on faceplate 23 is determined. In this embodiment, the type of energy source on faceplate 23 is an LED array 328, as discussed above. Processor 44 determines the presence of LED array 328 from Field 10 of record 204. Moreover, based on Field 8 of record 204, processor 44 sets the form of activation for LED array 328 to be either in the form of a pulse wave (PW) or a continuous wave (CW). In this example, a pulse wave at a rate of forty Hertz is used. In other embodiments other methods could be used for detecting the type of energy source and the form of activation. For example, control mechanism 300 can check the voltage across the connection to the energy source and make a determination based on the voltage value read. In yet other embodiments, the user can manually specify the activation form. These and other similar embodiments are within the scope of the invention.

Continuing with step 510, using record 204, target irradiance power, initial operating period and LED efficiency for LED 328 are obtained from Fields 5, 2 and 3 respectively of record 204. In this example target irradiance power for a cycle is about thirty J, the initial operating period is about ninety seconds, and the LED efficiency is about 12 mW/25 mA. Based on these values, the initial operating current is calculated. In this example, the initial operating current is chosen such that LED array 328 can deliver about thirty mJ in about ninety seconds. It is assumed that in this case, the initial operating current is calculated to be about 25 mA.

Having determined the properties of irradiance, at step 520 the user is warned that container 36 is to be activated. In this example, processor 44 delivers signals to power LED 316 and speaker 320 changing the color of power LED 316 to green and sounding two long beep tones. Processor 44 then causes a two second delay before continuing with method 400. As it is now apparent to those skilled in the art, in other embodiments, user warnings can be varied according to a number of criteria such as the amount of attention that needs to be drawn to the activation of pump 36, and the time necessary to prep the start of the treatment from the time switch 35 is pressed.

Continuing with method 400 at step 530, container 36 is activated. Control mechanism 300 activates container 36 by sending a signal to pump driver 344, which causes a certain amount of material 38 contained in container 36 to be pumped out. The number of activations or pulses is determined according to Field 8 of record 204. In this example, activation is for three pulses in accordance with the example record shown in Table I. In other embodiments, container 36 can be activated manually. For example, device 20 can generate a long beep for each manual activation to enable a user to release the correct amount of material 38 manually. In further embodiments, device 20 may be operated without the requirement of any material 38. These and other such embodiments are within the scope of the invention.

At step 540 the user is warned that energy source 30 is to be activated. In this example, processor 44 delivers a signal to speaker 320 sounding three long beep tones. Processor 44 then causes a two second delay before proceeding with method 400. As it is apparent to those skilled in the art, in other embodiments, user warnings can be varied according to a number of criteria such as the amount of attention that needs to be drawn to the start of the treatment, and the time necessary to prep the start of the treatment from the time switch 35 is pressed. Following the two second delay, the energy source is activated, signifying the start of the treatment cycle. In this embodiment, LED array 328 is activated by a driver current originating from energy source driver 336 of control mechanism 300. Moreover, cycle timer 212 is initialized to a value of zero.

At step 550 temperature reading is obtained from faceplate 23. In this example, processor 44 obtains a temperature reading from temperature sensing device 332. In this example, it is assumed that the reading is about forty one and a half degrees centigrade.

At step 570, cycle timer 212 is updated to reflect the amount of time that LED array 328 has been active so far during this cycle. Moreover, the power delivered so far in the cycle is updated by updating power counter 216. Prior to that, at step 560, a determination is made whether the temperature is within limits. In this example, the temperature reading obtained is compared to the upper and lower limits specified in fields 6 and 7 of record 204. Accordingly, a determination is made that the temperature is not within limits, and the drive level for LED array 328 is adjusted. Specifically, in this example, at step 565, array drive current and the duration of the cycle are adjusted. If the temperature read is too high, as it is in this case, LED array 328 drive current is reduced and cycle time is increased. If the temperature read is too low, LED array 328 drive current is increased and cycle time is decreased. As it is now apparent to those skilled in the art, these changes are done to maintain substantially the same target power delivery during a cycle while maintaining temperatures within specified limits. For example, where the temperature is too high, as it is in this example, reducing the drive current to LED array 328 reduces the heat output, allowing the heat to dissipate more readily. However, since the cycle time is increased, overall power delivered during the cycle can remain the same.

Continuing with method 400, at step 580, a determination is made as to whether the regimen is completed. In this example, the value of timer variable 212 is compared to the duration of cycles specified in Field 3 of record 204. If the cycle timer value is less, then the process is not complete, and method 400 loops back to step 550. In other embodiments other methods of determining the completion of the regimen can be used. For example, the power delivery can be used as a basis of determining a regimen's completion, deeming a regimen complete only if the target power has been delivered according to power counter 216. This and other such embodiments are within the scope of the invention. At this point in this example, it will be assumed that the cycle is not complete, causing step 550 to be performed again.

Continuing with the performance of method 400, after several performances of the loop that starts at step 550, a determination is made that the cycle is complete. Accordingly, step 590 is performed. At this step, the user is warned of the cycle's completion by sounding a four beep alarm through speaker 320. At step 590, the treatment is terminated. LED array 328 is turned off by cutting off its driving current. Device 20 is powered down and enters the low power mode where it awaits switch 35 to be pressed, at which point method 400 is performed again starting at step 410.

Figure 12:
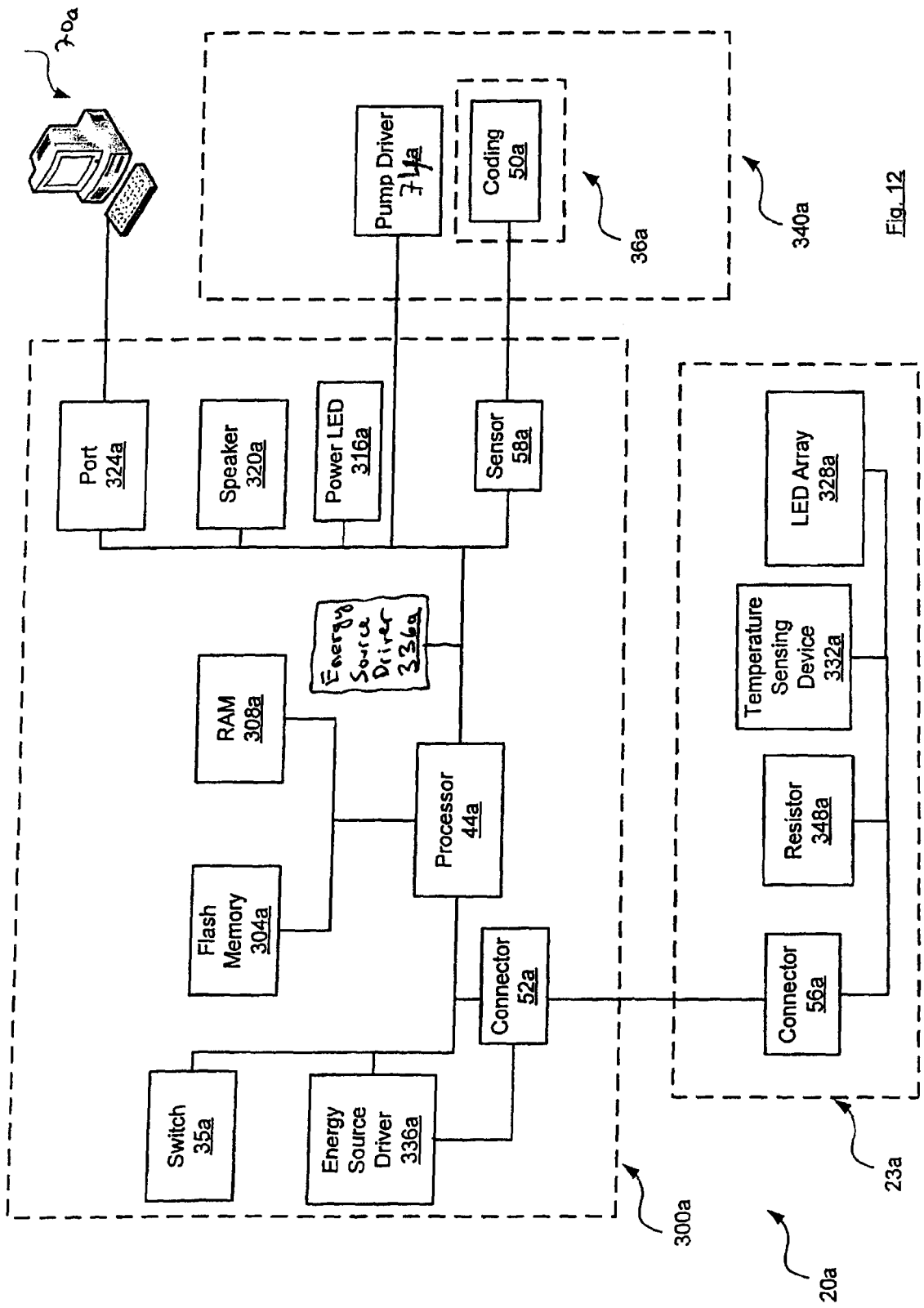
FIG. 12 is a block diagram showing electronic components in accordance with an aspect of the present invention where the faceplate does not include an EEPROM.

Performing method 400 using different embodiments of device 20 can result in performances that proceed differently than the example performance discussed above. For example, as shown in FIG. 12, method 400 can be performed by a device 20a to which a different faceplate, faceplate 23a that does not include an EEPROM 312. In this case, a resistor 348a is present on faceplate 23 to identify the type of faceplate. Device 20a is otherwise substantially the same as device 20 except that the reference numbers of components of device 20a include the suffix "a". Performance of method 400 using device 20a leads to several variations from the first example performance. One variation is that, at step 440, an EEPROM will not be detected, causing step 450 to be performed in place of step 460. At step 450, the type of faceplate is detected. The electrical coding used is in the form of a different voltage corresponding to different resistors used for faceplate types. Accordingly, data corresponding to record 204a is retrieved, by processor 44, in accordance with the faceplate type detected at step 450. Moreover, the record is retrieved from database 200a rather than from an EEPROM since there is no EEPROM present on faceplate 23a. The retrieved data is moved to RAM 308a for use during the delivery of the treatment.

Performing method 400 using device 20 which is at different operational states can also result in performances of method 400 that proceed differently than the example performance discussed above. For example, data contained in database 200 can be corrupted. Accordingly, at step 470 the data is determined to be invalid. Thus, step 475 is performed and an auditory alarm is sent to speaker 320, while power led 316 is signaled to turn red and flash. Following the alarm, method 400 advances to step 410 to determine whether the user has responded to the alarm by pressing switch 35 (for example, in response to the alarm, the user can reattach faceplate 23 to correct problems originating from improperly attached faceplate, or swap faceplates to correct problems originating from faulty faceplates). If so, method 400 is performed again, going through the same initialization and detection steps that brought method 400 to the validation step during the initial performance of method 400 that generated the alarm. If switch 35 is not pressed, processor 44 determines whether it is in low power mode at step 411. If so, it loops back to step 411. Otherwise, processor 44 determines whether it is time to enter a low power mode by first retrieving the value of timer variable 204 determining whether it has reached a value of zero at step 412. If it is determine that it is time to enter low power mode, device 20 enters the low power mode at step 413 until switch 35 is pressed. Otherwise, method 400 loops through steps 410, 411, and 412 until it is time to enter the low power mode or until switch 35 is pressed.

The device, method, and the material described herein can be used in combination with a medicament, active ingredient, or supplement.

For example, an acne treatment or prevention regimen using benzoyl peroxide and/or salicylic acid can comprise the application of a composition comprising benzoyl peroxide and/or salicylic acid to the affected area twice daily. The composition can comprise from about 0.5% to about 10% of benzoyl peroxide and/or salicylic acid, more preferably from about 0.8% to about 7% of benzoyl peroxide and/or salicylic acid, and even more preferably from about 1.0% to about 6.5% of benzoyl peroxide and/or salicylic acid by weight or volume is applied to the area of skin to be treated. The treatment can comprise starting with a composition comprising about 5% of benzoyl peroxide and/or salicylic acid and decreasing the dose in subsequent treatments to about 1 or 2% benzoyl peroxide and/or salicylic acid. Material 38 is then applied to the skin, and the skin is subsequently exposed to an energy source for a duration of time. Alternatively, material 38 can be applied to the skin before the composition.

According to another example of a method for treating or preventing acne of the present invention, material 38 itself comprises benzoyl peroxide and/or salicylic acid. Material 38 can comprise from about 0.5% to about 10% of benzoyl peroxide and/or salicylic acid, more preferably from about 0.8% to about 7% of benzoyl peroxide and/or salicylic acid, and even more preferably from about 1.0% to about 6.5% of benzoyl peroxide and/or salicylic acid by weight or volume. The treatment can comprise starting with material 38 comprising about 5% of benzoyl peroxide and/or salicylic acid and decreasing the dose in subsequent treatments to about 1 or 2% benzoyl peroxide and/or salicylic acid. The skin is subsequently exposed to the therapy device for a desired duration of time.

For the purposes of this example, the therapy device can be set to electromagnetic radiation in the range of about 380 to about 460 nm, more preferably in the range of about 395 to about 430 nm, and even more preferably in the range of about 405 to about 425 nm. The electromagnetic radiation can be about 415 nm. The device can alternatively or additionally comprise electromagnetic radiation in the range of about 460 to about 900 nm, more preferably in the range of about 550 to about 900 nm, and even more preferably in the range of about 570 to about 850 nm. The electromagnetic radiation can be about 630 nm.

The method for treating acne according to the present invention wherein material 38 comprises a desired amount of benzoyl peroxide and/or salicylic acid can be carried out about once a week, about once a day, or multiple times a day. Most preferably, the methods are carried out about once a day. The energy source can be applied to each section of the skin to be treated for a duration in the range of about 10 seconds to about 60 minutes, more preferably in the range of about 30 seconds to about 30 minutes, and even more preferably in the range of about 60 seconds to about 10 minutes each time the method is carried out. The duration can be about 90 seconds long. The dose received by each section of the skin to be treated can be in the range of about 5 Joules to about 60 Joules, more preferably in the range of about 10 Joules to about 50 Joules, and more preferably in the range of about 20 Joules to about 40 Joules. The dose can be about 30 Joules. The treatment can be applied for a period of about 1 to about 12 weeks, more preferably in the range of about 3 weeks to about 10 weeks, and most preferably in the range of about 6 weeks to about 8 weeks depending on the need of the individual. The treatment can also be applied, for the treatment of acne, by applying a treatment regimen by treating the face or affected area one to two times per day for one to two weeks, or until the bacteria populations are reduced to a desirable level, and then applying a maintenance regimen of one to two times per week.

However, depending on the severity and/or nature of the ailment and particular properties of the user's skin, much less time and/or total dose can be required.

It will be understood that other medicaments, active ingredients, or supplements can be used for the treatment or prevention of other indications using the device and material described herein.

It will be understood that medicaments, active ingredients, or supplements currently used, when used in conjunction with the device, material and methods of the present invention, can demonstrate an increase in effectiveness and therefore less of the medicament, active ingredient, or supplement and/or a shorter treatment time can be required to achieve a desirable result. For example, blue light (between 405 to 425 nanometers) can be absorbed by the skin and warm the skin sufficiently to increase the effectiveness of peroxide used for the treatment or prevention of acne. In such a case, the amount of peroxide or the duration of application of the peroxide currently recommended may be advantageously decreased. The blue light can also provide a synergistic effect by also being detrimental to the survival of any acne-causing bacteria residing on the skin. As is known in the art, P. acnes absorbs light from the ultraviolet region to about 430 nm, and also absorbs light at about 630 nm. Blue light phototherapy works for a majority of patients with P. Acne vulgaris. The bacteria is made up of an endogenous porphyrin which is a naturally occurring photosensitizer. This photosensitizer absorbs the blue light energy between about 405 to about 425 nanometers and forms a singlet oxygen which simply destroys the bacteria cell. Light administered to the skin at these wavelengths is usually absorbed by the epidermis and can penetrate it to a depth of at least about 1 mm.

The device, material, and methods of the present invention can also be used for photorejuvenation therapy. Photorejuvenation therapy can involve, for example, using the device with electromagnetic radiation including dominant emissions in the range of about 500 nm to about 1000 nm, more preferably in the range of about 550 nm to about 900 nm and even more preferably in the range of about 570 nm to about 650 nm. Most preferably dominant electromagnetic emissions are used at about 580 nm, about 630 nm, about 633 nm, about 660 nm, and/or emissions from in the range of about 800 nm to about 900 nm. The device can be further adapted to provide ultrasound or microwave energy which can have the effect of reducing inflammation, promoting cell repair, decreasing the appearance of fine lines and wrinkles, reducing pore size, reducing redness and improving skin texture. Alternatively, such ultrasound or microwave energy can be applied separately from the application of the device.

The device, material, and methods of the present invention can also be used to treat cellulite. The treatment of cellulite can involve, for example, using the device with electromagnetic radiation including dominant emissions in the range of about 500 nm to about 900 nm, more preferably in the range of about 550 nm to about 800 nm and even more preferably in the range of about 650 nm to about 750 nm. Other preferred electromagnetic radiation sources to treat cellulite include laser energy or LED energy at about 810 nm, or a combination of radiofrequency and infrared radiation. It will be noted that if laser energy or other potentially harmful radiation sources are used, the treatment may need to be supervised by a medical professional. The length of the treatments for cellulite can be in the range of about 10 seconds to about 180 minutes, more preferably in the range of about 20 seconds to about 60 minutes, and even more preferably in the range of about 30 seconds to about 10 minutes.

Depending on the ailment under treatment, parameters such as the frequency of treatments, the number of repetitions, and the duration of pulses can be adjusted so that the patient receives a total dose in the treated section of the skin of, for example, in the range of about 50 milliJ to about 100 J, more preferably in the range of about 500 milliJ to about 80 J and even more preferably in the range of about 1 J to about 50 J.

It will be recognized by those skilled in the art that the amount of pigment in a user's skin can affect the duration and/or intensity required for treatments using the device and material of the present invention. For example, the amount of pigment in skin is directly proportional to absorption of light at the surface of the skin. Therefore, there can be more absorption of light at the surface of darker skin types at depths of, for example, about 1-2 mm, and less penetration of light to depths of, for example, about 3-4 mm, as compared to fairer skin types. For treatments where deeper penetration is desired, duration and/or intensity of treatments can have to be increased for darker skin types.

The device and materials of the present invention can be used with treatment regimens known in the art. Any adjustments required to known treatment regimens would be apparent to those skilled in the art and should not require undue experimentation. The device and materials of the present invention can be used to treat such ailments as acne, arthritic pain, chronic pain, carpal tunnel syndrome, cellular damage, soft tissue injury, TMJ, diabetic neuropathy, neuralgia, aging skin, eczema, rosacia, actinic keratoses, seasonally affected disorder, inflammation, fine lines and wrinkles, cellulite, mucositis (oral mucosa), psoriasis, oral candida, oral cancer, wounds, soft tissue injuries such as capsulitis, bursitis, sprains, strains, hematomas and tendinitis, acute and chronic joint problems such as osteoarthritis, rheumatoid arthritis and ligament and tendon injuries, tendinitis, chronic pain such as post herpetic neuralgia, chronic back and neck pain, metatarsalgia, trigeminal neuralgia, brachial neuralgia, plantar fasciitis, and cellular damage.

Therapy using electromagnetic radiation can also be used to treat non-union and small bone fractures, herpes, apthous ulcers, leg ulcers, dermatitis, wound healing, burns, acute epididymitis, otorhinolaragngology, gynecology, obstetrics, superficial AP stimulation and tonification, cosmetic imperfections, among other things.

The device and materials of the present invention can be used to generally improve the appearance of skin. Any improvement of the appearance of skin can be temporary or somewhat permanent and can be measured in such terms as skin glow, clarity, texture, and smoothness.

In yet other variations, the contents of EEPROM 312 can be used for updating database 200. As an example, database 200 can be maintained in a separate persistent storage device such as Flash RAM or a hard drive included in device 20. Accordingly, persistent storage device can be updated with the contents of EEPROM 312, once faceplate 23 including EEPROM 312 is attached to device 20.

In yet other variations, control mechanism 300 can be implemented using different elements. For example, operations in control mechanism 300 can be carried out using an analog control circuit. In yet other variations, a programmable logic array (PLA) or a custom designed processor can be used as a processor 44. In further variations, other types of controller can be used as processor 44. In yet other variations, flash memory 304 can be replaced by a non volatile storage device such as an EEPROM, a read only memory (ROM), or a hard drive. In yet other variations, flash memory could be used in place of RAM 308. Moreover, storage devices included, such as EEPROM, ROM, RAM, hard drives, Flash RAM and others, could be removable such that the storage devices can be exchanged for updating the information accessible to device 20. In other variations, power driver 344 can be part of control mechanism 300. Moreover, different input and output devices can be used in place of a switch 35, power LED 316 and speaker 320. For example, different types of lights or multiple lights can be used in place of power LED 320. Speaker 320 can be replaced with a vibrator, or other device capable of getting a user's attention. Switch 35 can take the form of a push button switch or a touch sensitive switch.

In other variations, record 204 can be accessed directly from EEPROM 312 or flash-memory 304 during the operation of device 20, without the need to move the data into RAM 308. In yet other variations, only a portion of the data corresponding to a record or multiple records can be present in EEPROM 312, the remainder being contained in database 200. In further variations, a control mechanism can also reside on faceplate 23, allowing the performance of method 400 or part thereof on faceplate 23.

In other variations, Method 400 can be altered such that different number of beeps, and light signals and wait times are used for informing the user of warnings and alarms. For example, additional LEDs can be used in place of sound alarms. Or different types of lights and colors can be used. Intensity, instead of color of LEDs can be altered or different color changes can be used. Duration of waits times can also vary.

Figure 13A:
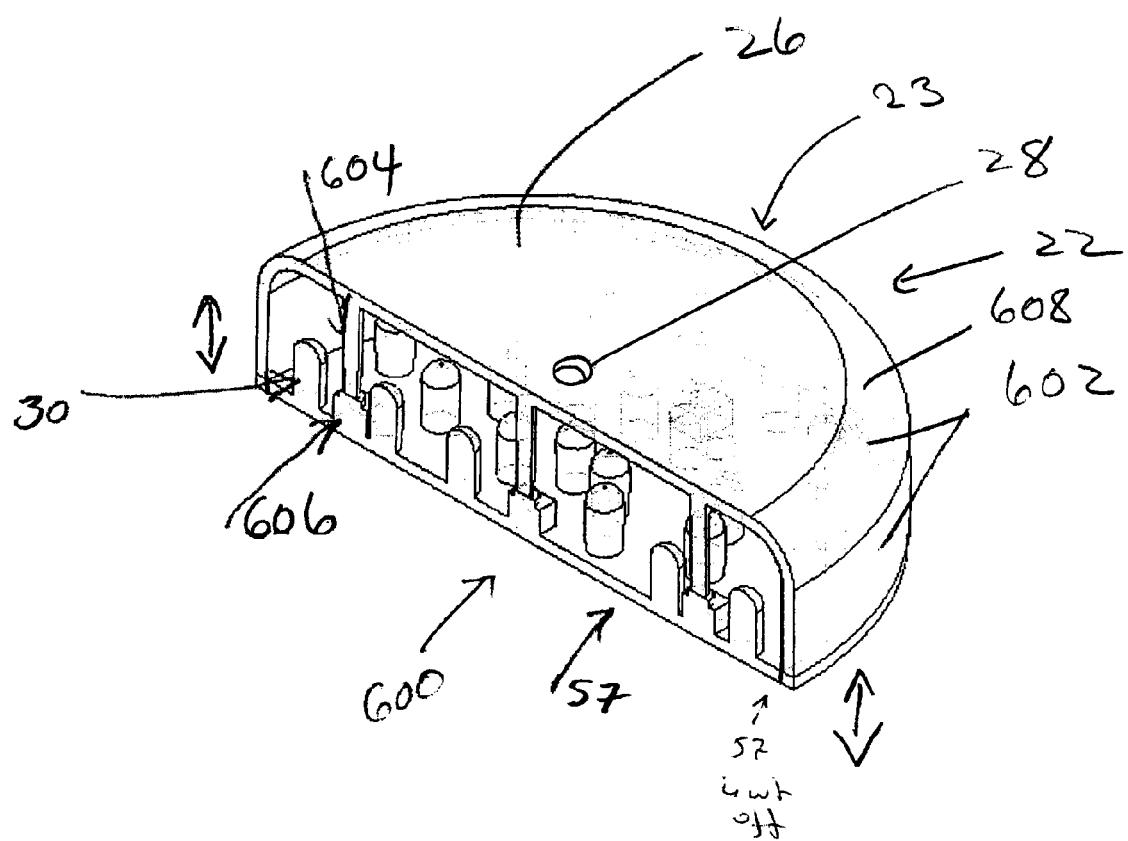
Figure 13D:
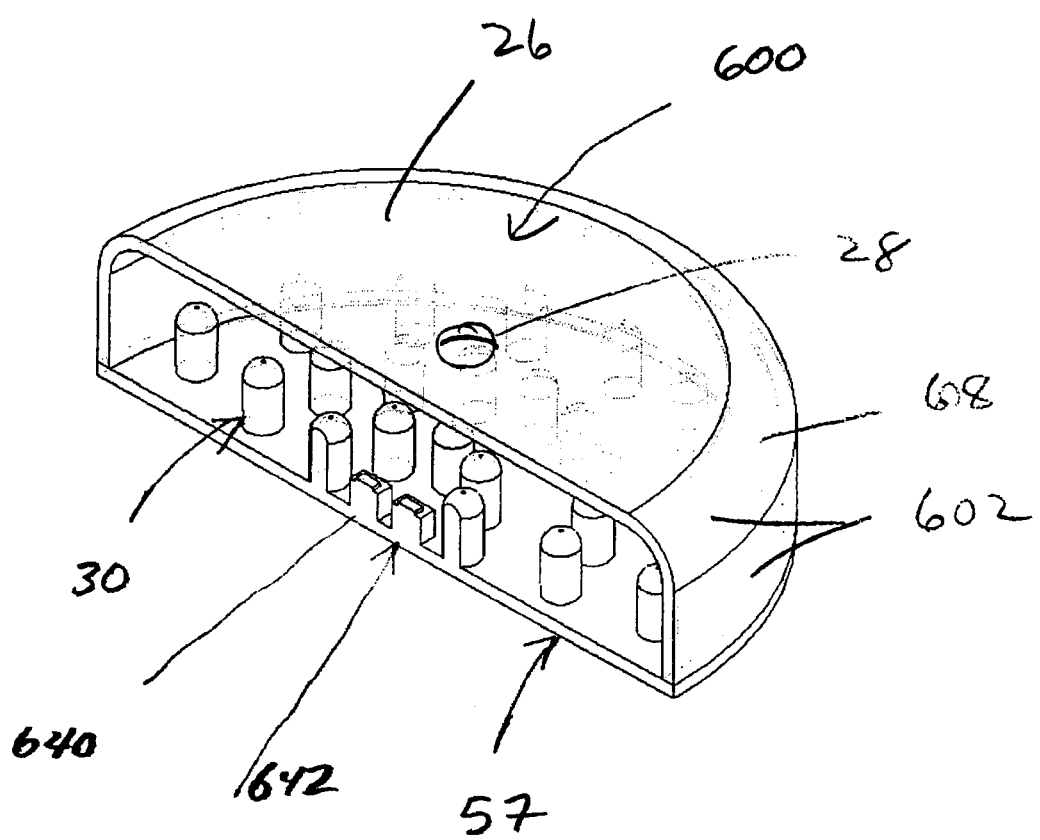
Figure 13E:
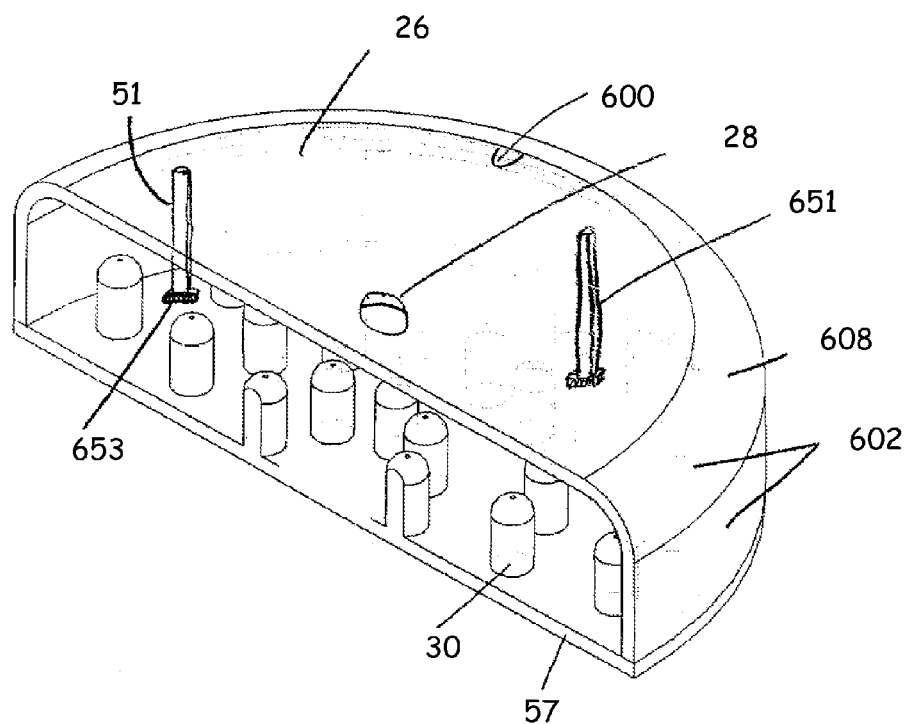
Figure 14:
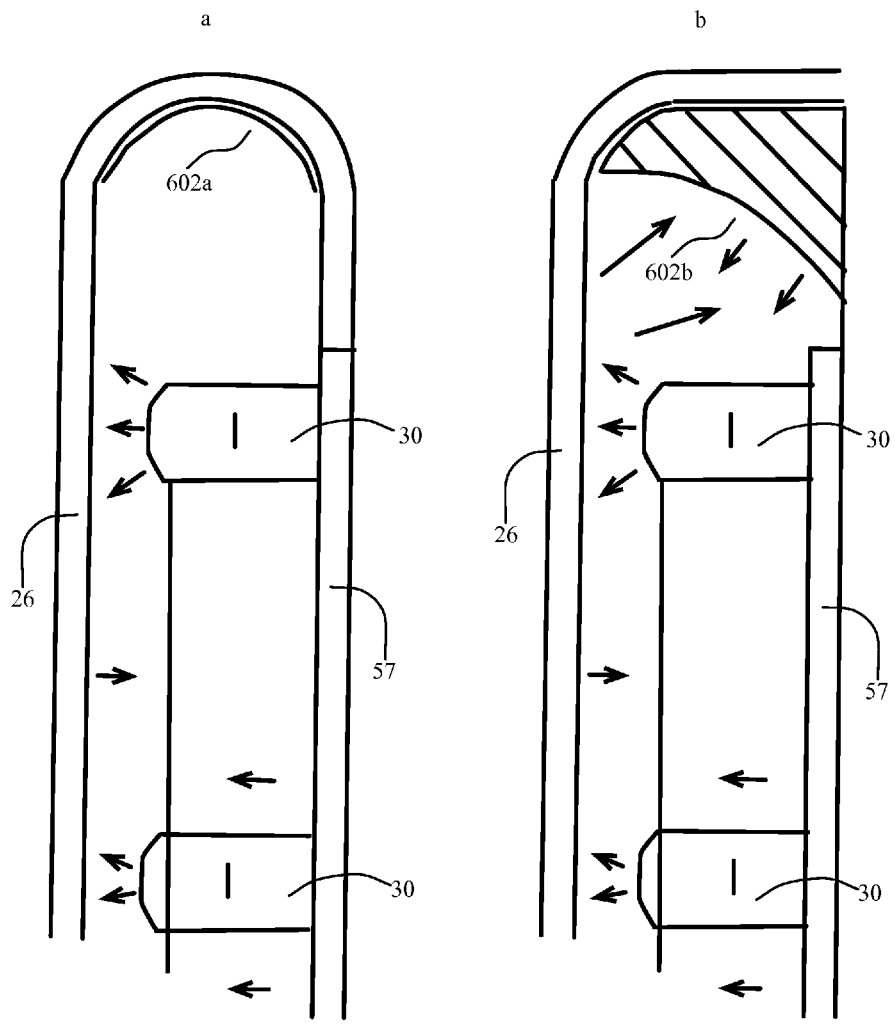
FIGS. 14 a) and b) are a cross-sectional views of different embodiments of heads for a therapy device incorporating a radiation shield in accordance with the present invention.

Referring now to FIGS. 13-16, various embodiments of improvements to the design of head 22 and related method are depicted. Such improvements are provided to reduce the likelihood of a user being harmfully exposed to radiation emanating from head 22 and to improve the functionality of the device. It will be understood that head 22 as depicted in any one of FIGS. 13-14 is intended to be incorporated as part of the therapy device 20 and utilized as part of the method 400 described earlier and shown in the Figures (subject to certain modifications where applicable as described below). The improvements depicted in FIGS. 13-16 may also be incorporated into other devices and methods where it is desirable for instance to limit certain operations of the device. The description provided herein is in no way intended to limit application to such other devices.

A more detailed description of the improvements depicted in FIGS. 13-16 is provided below. Corresponding reference numerals are used to refer to corresponding elements of the head 22 as described above.

In each of FIGS. 13-14 head 22 includes an outer surface 26, one or more apertures 28 for allowing the distribution of material 38 through outer surface 26 and energy source 30 for emitting electromagnetic radiation. Head 22 further includes substrate 57 which may comprise a printed circuit board (PCB) or an equivalent functional structure. PCB 57 has a surface that can reflect energy emitted from energy source 30. Such a surface may be constructed by covering or coating the top of PCB 57 with reflective material such as a white colored material where the energy source 30 emits electromagnetic radiation within the visible spectrum, a gold colored material where the energy source emits electromagnetic radiation within the infrared spectrum or a silver colored material where the energy source emits electromagnetic radiation within the ultraviolet spectrum. While the depicted embodiment includes outer surface 26 it will be understood that head 22 may be used without outer surface 26 or without material 38.

In a preferred embodiment, head 22 is comprised of faceplate 23 and baseplate 25 with faceplate 23 being depicted in FIGS. 13-14. In other embodiments, faceplate 23 and baseplate 25 may be integrally formed as part of a uniform structure for head 22. For convenience, the term head 22 will be used with the understanding that the embodiment may be either a head 22 or a faceplate 23 portion of head 22.

In each of FIGS. 13A-13E, head 22 further includes a proximity sensor 600 and a radiation shield 602. Proximity sensor 600 operates to signal proximity of the head 22 to the skin in order to safely control activation of the energy sources 30. Further description of different embodiments of proximity sensor 600 is provided below. Radiation shield 602 surrounds the energy sources 30 in order to reduce the likelihood of radiation emanating from the sides of the head 22 and to reflect energy emitted from energy source 30. As shown in FIG. 14a, radiation shield 602 may be constructed by covering or coating the side portions of faceplate 23 with reflective and opaque material 602a. Alternatively, as depicted in FIG. 14b, the radiation shield can be constructed from a material 602b, separate from and disposed within head 22. Radiation shield 602 may be formed of an opaque plastic or any other material that is suitable for shielding radiation from being transmitted from the sides of the head 22. Moreover, the material forming reflective shield 602 can also be reflective, such as a white colored plastic where the energy sources 30 emit electromagnetic radiation within the visible spectrum, a gold colored material where the energy source emits electromagnetic radiation within the infrared spectrum or a silver colored material where the energy source emits electromagnetic radiation within the ultraviolet spectrum.

Accordingly, the reflective surface of PCB 57 in combination with the reflective surface of radiation shield 602 can achieve radiation recycling, increasing the treatment fluence by up to 300% to 400% in comparison to that when no reflective surfaces are present. Moreover, index matching may also increase fluence by another 20%

Referring back to FIG. 13A, one embodiment of proximity sensor 600 operates electro-mechanically. Accordingly, the pressure of applying faceplate 23 to the treatment surface is detected and used in controlling the activation of energy sources 30. The pressure detection can be achieved by placing a pressure sensing device between the displaceable face plate 23 and PCB 57. In one embodiment, the pressure detection could be implemented by using a boss extension 604 and a resilient or spring loaded push button switch 606 which is electrically connected to control mechanism 300. When the faceplate 23 is placed into contact with a surface such as skin, boss extension 604 is displaced towards push switch 606 and push button switch 606 generates a signal in response to the displacement. Push button switch is attached to PCB 57, and through the circuitry in PCB 57 is in communication with control mechanism 300 and processor 44.

It will also be understood that although a push button switch 606 is identified, other electromechanical switches may be utilized such as a strain gauge or a pressure sensitive film or touch plate located on outer surface 26 or on an outer edge 608 of radiation shield 602.

Referring to FIG. 13B, another embodiment of proximity sensor 600 operates by measuring resistance. A conductive material 618 such as a conductive polymer is applied to outer surface 26 and/or outer edge 608 of radiation shield 602 and a lead 619 extends between conductive material 618 and the PCB 57, and accordingly, through the circuitry contained within PCB 57, establish an electrical connection with processor 44. In a preferred embodiment, the conductive polymer applied includes at least two contacts 620 which draw power from lead 619. It is typically considered that 10 contacts would be adequate. The contacts are located so as to not obstruct the delivered radiance, although in some embodiments some obstruction may occur. Contacts 616 are biased with a Safety Extra Low Voltage (SELV) voltage and can allow a current to pass between each adjacent contact 620 along conductive material 618. The optionally present current can be as small as 10 uA to avoid any uncomfortable electrical sensations by the user when their skin is in contact with the head 22.

When head 22 engages or is proximate to a skin surface, resistance between contacts 620 changes as a result of the resistance impacted by the skin. Accordingly, a voltage drop is experienced, the drop in voltage being detectable by processor 44 which is in communication with the contacts 620 Thus, processor 44 can monitor, in a manner that is known to those skilled in the art, the voltage being received from the contacts 620 and activate or deactivate the supply of energy to energy sources 30 accordingly.

Referring to FIG. 13C, another embodiment of proximity sensor 600 operates by measuring capacitance. Proximity sensor 600 includes antenna 630 or other capacitive sensor (which may be a wire or another suitable conductive material) that is moulded into or fastened to outer surface 26 or to outer edge 608 of face plate 23. In this embodiment, the proximity sensor 600 includes a sensing circuitry that is in communication with processor 44. Sensing circuitry can cause a constant voltage to be applied to the antenna 620 and detect any changes in capacitance in a manner that is known to those skilled in the art. For example, as described in the QT113 data sheet by Quantum Research Group, "Kirchoff's Current Law" can be used to detect the change in capacitance of the electrode or antenna. According to the Kirchoff's Current law, as applied to capacitive sensing, the antennae 630's field current completes a loop, returning back to its source in order for capacitance to be sensed; thus the Kirchoff's Current Law applies to capacitive field flows. By implication, the signal ground and the target object both are coupled together in some manner for a capacitive sensor to operate. Although actual hardwired ground connections do work capacitive coupling to ground is also possible.

The sensing circuitry can use bursts of charge-transfer cycles to acquire a signal. The antenna or external electrode acts as a sense capacitor and this capacitance is compared to an internal fixed capacitor using capacitance charge methods.

When the head 22 is positioned against or proximate to a skin surface, the skin causes a disturbance in the capacitive field around the antenna 630, and a signal is transmitted by the sensing circuitry to processor 44, which can then cause the activation or deactivation of the energy source 30 accordingly.

Referring to FIG. 13D, another embodiment of proximity sensor 600 operates by using optical or sonar means for detecting proximity to a skin surface. Proximity sensor 600 includes receiver 640 and transmitter 642 which are both electrically connected to the circuitry included in PCB 57. Transmitter 642 emits a light or sound signal that reflects off a skin surface and is received by the receiver 640. Receiver 640 communicates with processor 44 via the circuitry included in PCB 57 to activate or deactivate the supply of energy to the energy sources 30 in accordance with a predetermined proximity to the skin.

Transmitter 642 emits light or sound that is preferably undetectable to the human eye or ear and does not cause injury or discomfort to the human eye or ear. Transmitter 642 may for instance emit light in any range, but is optimally configured to transmit in the infra-red range, known to those skilled in the art to be between 800-950 nm. Receiver 640 may then, for instance, be optimally configured to respond only to light in the range emitted by the transmitter 642, and is not responsive to the light emitted by energy source 30. As understood by those of ordinary skill in the art, the detector 640 may be configured to indicate the presence of the skin within a predetermined distance. Such distance is optimally between 0.5-10 cm.

Referring to FIG. 13E, another embodiment of proximity sensor 600 operates by measuring temperature. Proximity sensor 600 includes thermal conductor 651 and thermal transducer 653 (or conductor 51 and transducer 53 as described earlier) disposed on or in outer surface 26 or outer edge 608 of radiation shield 602. When head 22 is proximate to or engaged with the skin, thermal conductor 651 will conduct heat either away from or towards the thermal transducer 653. When a sufficient amount of heat is displaced, thermal transducer 653 provides a signal to PCB 57 to activate or deactivate the supply of energy to energy source 30.

As known to those skilled in the art, thermal transducer 653 can be configured to provide the signal to processor 44 when various changes in temperature are detected, such change being detected over a given amount of time. Optimally, thermal transducer 653 is responsive to small temperature changes in a short amount of time, such temperature change optimally being between [1-3 degrees] and such time being between [0.1-2.0 seconds].

Figure 15:
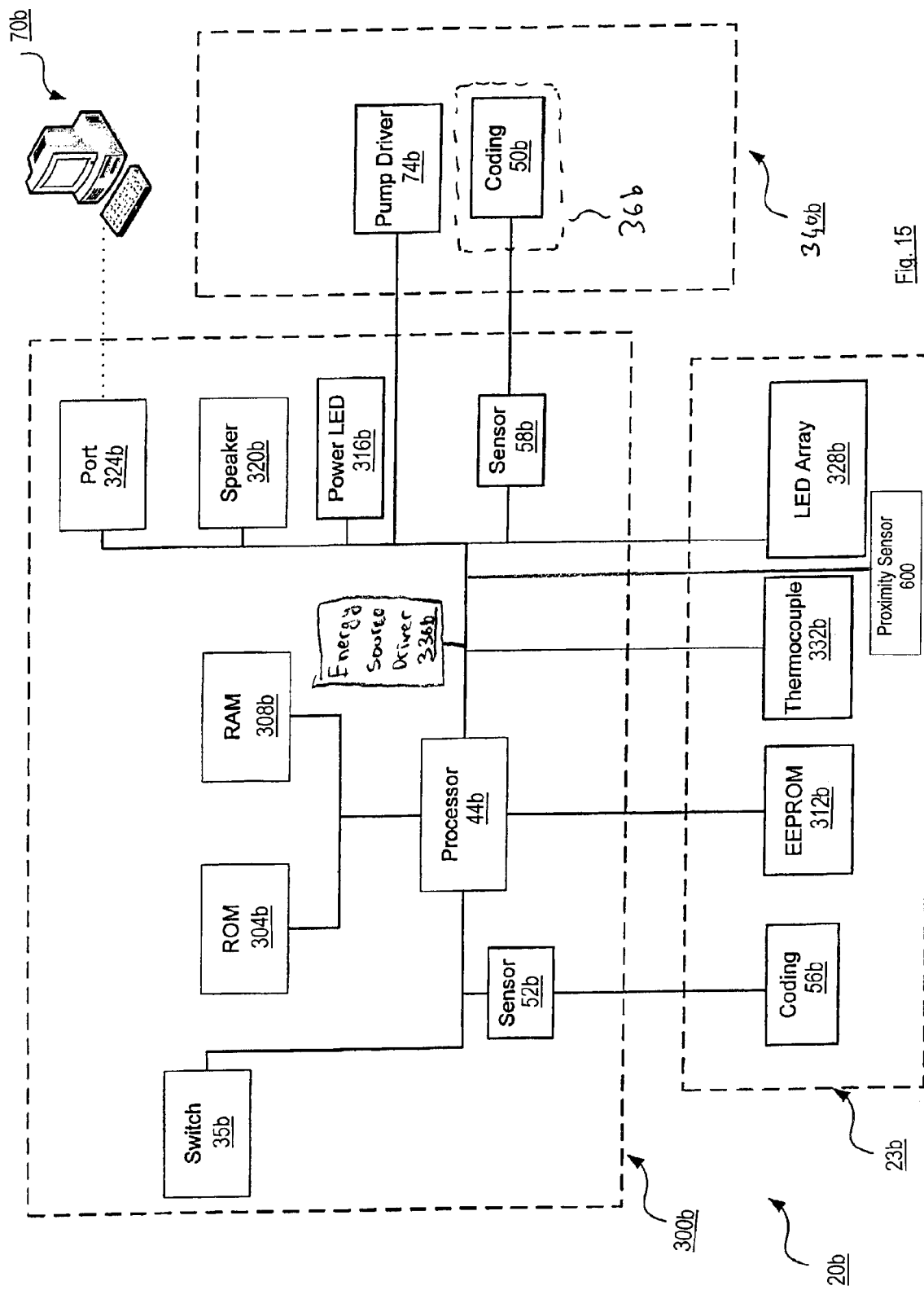
FIG. 15 is a block diagram showing electronic components in accordance with one aspect of the present invention.

Referring now to FIG. 15, a block diagram of certain components of device 20b are shown according to an embodiment of the invention. In this embodiment, device 20b includes a proximity sensor 600 on faceplate 23b. Proximity sensor 600 is present on faceplate 23b to help control the activation of the energy sources 30 based on a proximity of faceplate 23 to a treatment surface such as the skin. Device 20b is otherwise substantially the same as device 20 except that the reference numbers of components of device 20b include the suffix "b". Proximity sensor 600 is operably connected to control mechanism 300, and is thus operable to transmit signals to processor 44b, the signals being interpretable by processor 44b and corresponding to the proximity of faceplate 23 to a treatment surface. As described above, in some embodiments, proximity sensor 600 can include additional sensor circuitry to facilitate the detection and transmission of signals.

Figure 16:
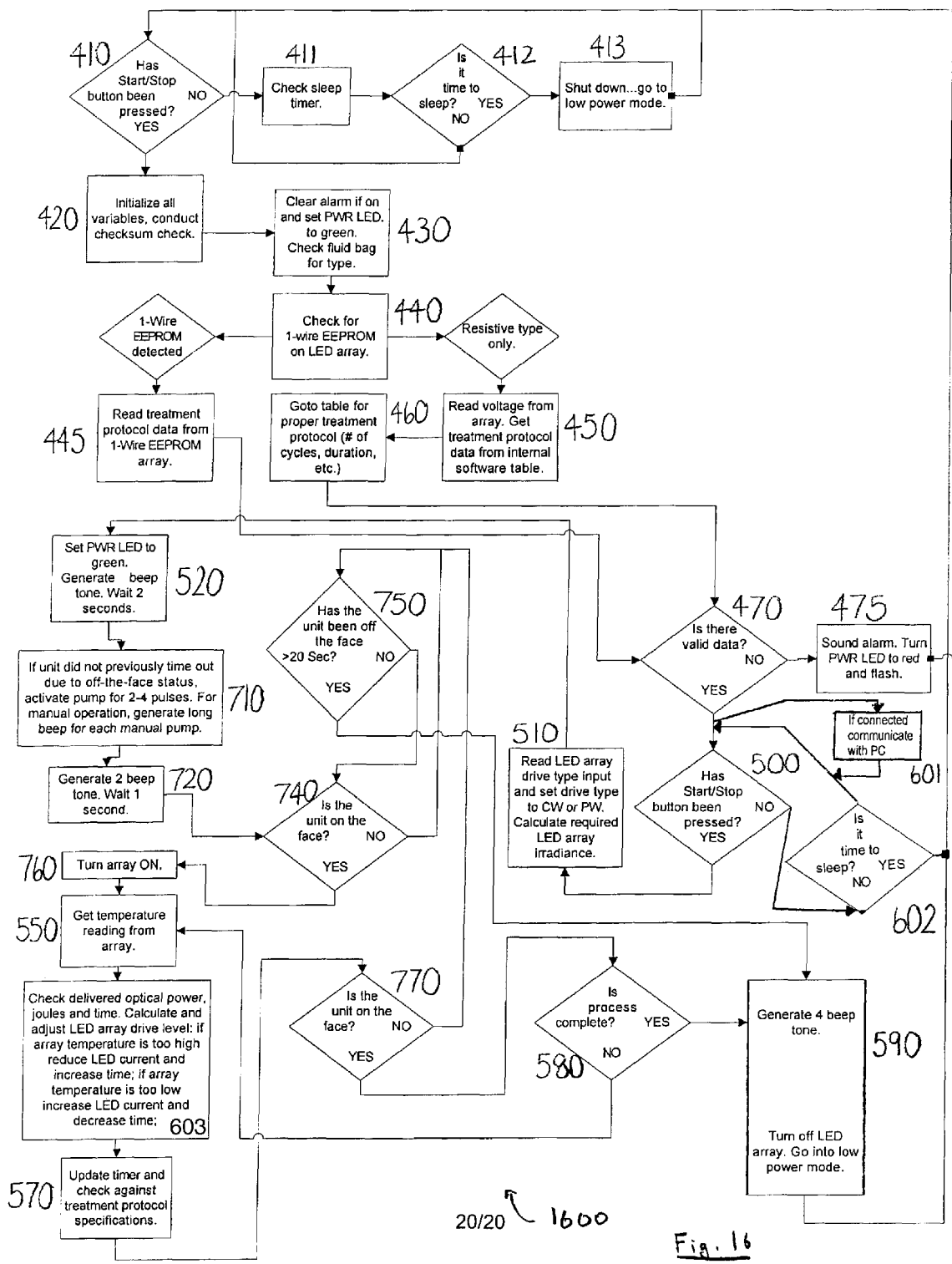
FIG. 16 is a flow chart showing a method for reducing exposure to harmful electromagnetic radiation in accordance with the present invention.

Referring to FIG. 16, a method for proximity controlled activation of energy sources 30b is indicated generally at 1600. In order to assist in the explanation of the method, it will be assumed that method 1600 is performed using device 20b. Furthermore, the following discussion of method 1600 will lead to a further understanding of device 20b and its various components. (However, it is to be understood that device 20b and/or method 1600 can be varied, and need not work exactly as discussed herein in conjunction with each other, and that such variations are within the scope of the invention).

Method 1600 is similar to method 400, except for the steps with the reference numbers in the 600s or 700s. Specifically, steps with the reference numbers in the 600s correspond to a compilation of a number of steps in method 400, so compiled as to simplify the illustration of method 1600. More specifically, step 601 corresponds to steps 480, 490, and 495 in method 400. Moreover, 602 corresponds to detection steps of 501, 502 and 503 in method 400. Additionally, step 603 corresponds to steps 560 and 564 where the current delivered to energy sources 30, as well as other parameters are adjusted based on detected skin temperature and other measures of power delivery.

Steps with reference numbers in the 700s are, on the other hand, steps that are only found in method 1600 and are used in implementing proximity controlled activation of energy sources 30. Accordingly, the below description of method 1600 focuses on the performance of these steps.

The current performance of method 1600 is initiated, in a similar manner to the performance of method 400, by pressing switch 35b to turn the device on while device 20 is in a low power mode. It will now be apparent to those skilled in the art that steps of method 1600 up until and including step 520 are substantially the same as the corresponding steps of method 400 described above. Thus, the description of the example performance of method 1600 is continued at step 520, with the assumption that the example performance of method 1600 up until step 520 is substantially the same as the example performances of method 400 described previously. Accordingly, at step 520 the user is warned that container 36b is to be activated. In this example, processor 44b delivers signals to power LED 316b and speaker 320b changing the color of power LED 316b to green and sounding two long beep tones. Processor 44b then causes a two second delay before continuing with method 400. As it is now apparent to those skilled in the art, in other embodiments, user warnings can be varied according to a number of criteria such as the amount of attention that needs to be drawn to the activation of pump 36b, and the time necessary to prep the start of the treatment from the time switch 35b is pressed.

Continuing with method 1600, container 36b is activated. This activation is performed only if the device 20b had not timed out due to having been placed farther away for the treatment surface then a desirable proximity, thus preventing the device from delivering too much material 38b. Control mechanism 300b activates container 36b by sending a signal to pump driver 344b, which causes a certain amount of material 38 contained in container 36 to be pumped out. The number of activations or pulses is determined according to Field 8 of record 204b, as with the performance of method 400. In this example, activation is for three pulses. In other embodiments, container 36b can be activated manually. For example, device 20b can generate a long beep for each manual activation to enable a user to release the correct amount of material 38b manually. In further embodiments, device 20b may be operated without the requirement of any material 38b. These and other such embodiments are within the scope of the invention.

At step 720, the user is warned that energy source 30b is to be activated. In this example, processor 44b delivers a signal to speaker 320b sounding two long beep tones. Processor 44b then causes a one second delay before continuing with method 1600. As it is apparent to those skilled in the art, in other embodiments, user warnings can be varied according to a number of criteria such as the amount of attention that needs to be drawn to the start of the treatment, and the time necessary to prep the start of the treatment from the time switch 35b is pressed. Following the two second delay, the energy source is activated, signifying the start of the treatment cycle. In this embodiment, LED array 328b is activated by a driver current originating from energy source driver 336b of control mechanism 300b. Moreover, cycle timer 212b is initialized to a value of zero.

At step 740, proximity sensor 600, being any proximity sensor 600 including those disclosed and described according to FIGS. 13A-13E, is monitored. If a desired proximity or engagement with the user's skin is not detected by processor 44b, the method continues to Step 750. Otherwise the method progresses to step 760, the performance of which is described below. At Step 750, a timeout counter maintained by control mechanism 300b is accessed by processor 44b, the timeout counter having a value representative of the amount of time the device 20b has been off the treatment surface. This counter is compared, by processor 44, with a maximum timeout variable maintained by control mechanism 300 and the value stored by the maximum timeout variable representing the maximum allowable time device 20b can be off the treatment surface. The value contained the maximum timeout is configurable, but optimally represents a time period in the range of 1-20 seconds. If the value represented by the timeout counter is less than the value of the maximum timeout variable, the method continues with step 740, looping between steps 740 and 750 until either the device 20b is brought within the desired proximity of the face or until the counter exceeds the value in the maximum timeout variable, causing a timeout to occur. If the device 20b is brought within the desired proximity before a timeout occurs, the method continues at step 760 where the energy sources 30 are turned on, after which step 550 is performed. Where a timeout occurs, the method continues to Step 590, where the device 20b is brought into the low power mode in a manner as described previously.

At step 550 temperature reading is obtained from faceplate 23. In this example, processor 44b obtains a temperature reading from temperature sensing device 332b. At step 603 the current delivered to energy sources 30, as well as other parameters are adjusted based on the detected skin temperature in a manner described above during the example performance of steps 560 and 565 of method 400

Continuing with method 1600, at step 570, the necessary internal parameters are adjusted to reflect the progress of treatment delivery. At step 740, proximity sensor 600, being any proximity sensor 600 including those disclosed and described according to FIGS. 13A-13E, is monitored. If a desired proximity or engagement with the user's skin is not detected by processor 44b, the method continues to Step 750. Otherwise the method progresses to step 580, where the completion of the treatment process is determined. Where the method advances to step 750, the method loops between steps 750 and 740, in the manner described above, until either the device is brought within the desired proximity of the treatment surface or until the device 20b is powered down due to a timeout. The desired proximity range is adjustable by appropriately configuring proximity sensor 600 and control mechanism 300 such that when the treatment surface is at the desired proximity for the treatment type being provided processor 44b can detect this proximity by monitoring proximity sensor 600.

The above detailed description is of the best presently contemplated mode of carrying out the invention. This description is not to be taken in a limiting sense, but is made merely for the purpose of illustrating the general principles of the invention. The scope of the invention is best defined by the appended claims.

The invention claimed is:

1. A treatment system comprising:
a body adapted to be handheld;
a controller disposed within said body adapted for receiving information from a head and in response thereto, controlling application of a desired treatment;
a plurality of heads adapted for being interchangeably mounted to said body, each said head including an energy source for emitting electromagnetic radiation having desired characteristics associated with a desired treatment;
each said head also including one or more connectors adapted for removable connection with one or more corresponding connectors disposed on said body for facilitating transmission of electrical power from said body to said head for powering said energy source and for facilitating communication of information between said head and said controller; and
at least one of said heads including a proximity sensor adapted for sensing proximity of said head to a surface, said proximity sensor communicating with said controller to control said emission of electromagnetic radiation in accordance with the sensed proximity of said head to said surface.

2. A treatment system as claimed in claim 1, wherein at least one of said plurality of heads includes a temperature sensor, said temperature sensor being adapted for sensing the temperature of an area proximate to said head during the application of said desired treatment, said temperature sensor communicating with said controller to facilitate control of said emission of electromagnetic radiation in accordance with the temperature sensed by said temperature sensor.

3. A treatment system as claimed in claim 2 wherein the controller is adapted to control operation of the energy source when the temperature sensed by said temperature sensor is outside pre-specified limits.

4. A treatment system as claimed in claim 2 wherein the temperature sensor is a p-n junction diode.

5. A treatment system as claimed in claim 1 wherein said one or more connectors disposed on each of said heads includes an identifier adapted for communicating identification information concerning the characteristics of said head to said controller disposed on said body.

6. A treatment system as claimed in claim 1 wherein the proximity sensor is adapted to sense when said head engages a surface and said sensor is adapted to communicate with said controller to control emission of electromagnetic radiation when said head engages said surface.

7. A treatment system as claimed in claim 1 wherein the energy source for at least one of said heads comprises at least one light emitting diode.

8. A treatment system as claimed in claim 1 wherein the energy source for at least one of the heads has at least one peak wavelength selected from about 410, 415, 580, 630, 660, 663, 680, 800, 810, 820, 830, 840, 850, and 900 nm.

9. A treatment system as claimed in claim 1 wherein the energy source for at least one of the heads comprises at least one peak wavelength having a band width of about 40 nm, more preferably about 20 nm.

10. A treatment system as claimed in claim 1 wherein the energy source for at least one of the heads has a peak wavelength of about 415 nm and a bandwidth of about 20 nm.

11. A treatment system as claimed in claim 1 wherein the energy source for at least one of the heads operates in a pulsed manner when activated.

12. A treatment system as claimed in claim 1 wherein the controller includes a storage device adapted to maintain regimen data, the controller being operable to control the device in accordance with the regimen data.

13. A treatment system as claimed in claim 12 wherein the controller is adapted to control the emission of radiation from the energy source at a power level and for a period of time in accordance with the regimen data.

14. A treatment system as claimed in claim 12 further comprising an interface adapted to conduct communications with a computing device for updating the regimen data.

15. A treatment system as claimed in claim 12 further comprising an interface adapted to conduct communications with a computer network having at least one server for updating the regimen data.

16. A treatment system as claimed in claim 12 wherein the storage device is removable.

17. A treatment system as claimed in claim 12 wherein said treatment system is further adapted to maintain, in said storage device, logging data representing a usage of the treatment system.

18. A treatment system as claimed in claim 1 wherein at least one of said plurality of heads includes an energy reflective layer disposed proximate to the energy source for reflecting electromagnetic radiation towards said surface.

19. A treatment system, as claimed in claim 1, further comprising:
   a faceplate and a baseplate and wherein the faceplate is adapted for being removably mounted to a corresponding baseplate disposed on said body.

* * * * *